(12) United States Patent
Iaccino et al.

(10) Patent No.: US 9,994,499 B2
(45) Date of Patent: *Jun. 12, 2018

(54) PRODUCTION OF CYCLIC C$_5$ COMPOUNDS

(71) Applicant: ExxonMobil Chemical Patents Inc., Baytown, TX (US)

(72) Inventors: Larry L. Iaccino, Seabrook, TX (US); Jeremy W. Bedard, Houston, TX (US); Wenyih F. Lai, Bridgewater, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/288,378

(22) Filed: Oct. 7, 2016

(65) Prior Publication Data

US 2017/0121246 A1 May 4, 2017

Related U.S. Application Data

(60) Provisional application No. 62/250,689, filed on Nov. 4, 2015.

(51) Int. Cl.
| | |
|---|---|
| *C07C 5/327* | (2006.01) |
| *C07C 5/32* | (2006.01) |
| *C07C 5/333* | (2006.01) |
| *C07C 5/373* | (2006.01) |
| *B01J 29/44* | (2006.01) |
| *B01J 29/46* | (2006.01) |

(52) U.S. Cl.
CPC .............. *C07C 5/373* (2013.01); *B01J 29/44* (2013.01); *B01J 29/46* (2013.01); *C07C 2101/10* (2013.01); *C07C 2529/44* (2013.01); *C07C 2529/46* (2013.01)

(58) Field of Classification Search
CPC ............ C07C 5/327; C07C 5/32; C07C 5/333
USPC ........................................ 585/365, 366, 369
See application file for complete search history.

(56) References Cited

U.S. PATENT DOCUMENTS

| | | |
|---|---|---|
| 2,438,398 A | 3/1948 | Kennedy et al. |
| 2,438,399 A | 3/1948 | Kennedy et al. |
| 2,438,400 A | 3/1948 | Hetzel et al. |
| 2,438,401 A | 3/1948 | Kennedy et al. |
| 2,438,402 A | 3/1948 | Kennedy et al. |
| 2,438,403 A | 3/1948 | Kennedy et al. |
| 2,438,404 A | 3/1948 | Hetzel et al. |
| 2,982,798 A | 5/1961 | Hachmuth et al. |
| 3,953,368 A | 4/1976 | Sinfelt |
| 4,886,926 A | 12/1989 | Dessau et al. |
| 5,192,728 A | 3/1993 | Dessau et al. |
| 5,254,787 A | 10/1993 | Dessau |
| 5,284,986 A | 2/1994 | Dessau |
| 5,633,421 A | 5/1997 | Iezzi et al. |
| 9,006,125 B2 | 4/2015 | Levin et al. |
| 2010/0234657 A1 | 9/2010 | Takamatsu et al. |
| 2015/0025283 A1 | 1/2015 | Cheng et al. |

FOREIGN PATENT DOCUMENTS

| | | |
|---|---|---|
| CN | 1810743 A | 8/2006 |
| DE | 2535809 | 3/1976 |
| WO | WO 89/04818 | 6/1989 |

OTHER PUBLICATIONS

U.S. Appl. No. 62/250,675, filed Nov. 4, 2015, Iaccino et al.
U.S. Appl. No. 62/250,681, filed Nov. 4, 2015, Iaccino et al.
U.S. Appl. No. 62/250,688, filed Nov. 4, 2015, Iaccino et al.
U.S. Appl. No. 62/250,689, filed Nov. 4, 2015, Iaccino et al.
Briceno, S. et al. "*Reduction Catalitica de NOx con Pt soportado sobre zeolitas MFI modificadas con Cu, Co, Fe, Mn.*" Avances en Quimica, 2008, vol. 3, No. 1, pp. 21-26. [abstract].
Bricker, J.C., "*Advanced Catalytic Dehydrogenation Technologies for Production of Olefins*," Topics in Catalysis, 2012, vol. 55, pp. 1309-1314.
Fel'dblyum, V.S., et al., "*Cyclization and Dehydrocyclization of C$_5$ Hydrocarbons over Platinum Nanocatalysts and in the Presence of Hydrogen Sulfide,*" Doklady Chemistry, 2009, vol. 424, Part 2, pp. 27-30.
Kanazirev, V., et al., "*Conversion of C$_8$ Aromatics and n-Pentane Over Ga$_2$O$_3$/HZSM-5 Mechanically Mixed Catalysts*", Catalysis Letters, 1991, vol. 9, pp. 35-42.
Kennedy, R.M., et al., "*Formation of Cyclopentadiene from 1,3-Pentadiene,*" Industrial and Engineering Chemistry, 1950, vol. 42, No. 3, pp. 547-552.
Kumar, S., et al. "*Metal Exchanged ZSM-5 Zeolite Based Catalysts for Direct Decomposition of N$_2$O*", Catalysis Letters, Kluwer Academic Publishers-Plenum Publishers, 2009, vol. 132, No. 1-2, pp. 248-252.
Li, X., et al., "*Catalytic Dehydroisomerization of n-alkanes to Isoalkenes,*" Journal of Catalysis, 2008, vol. 255, pp. 134-137.
Lopez, C.M., et al., "*n-Pentane Hydroisomerization on Pt Containing HZSM-5, HBEA and SAPO-11,*" Catalysis Letters, 2008, vol. 122, pp. 267-273.
Marcinkowski, T.E., "*Isomerization and Dehydrocyclization of 1,3-Pentadiene,*" Retrospective Theses and Dissertations, 1979, Paper 433, pp. 1-110.
Pfaff, C., et al., "*Pt-Cu/ZSM-5 for Removal of Nitrates from Drinking Water*", Reaction Kinetics and Catalysis Letters, 2002, vol. 77, No. 2, pp. 263-266.
Vora, B.V., "*Development of Dehydrogenation Catalysts and Processes,*" Topics in Catalysis, 2012, vol. 55, pp. 1297-1308.
Xinghua, Z.,et al., "*Aqueous-Phase Catalytic Process for Production of Pentane from Furfural Over Nickel-Based Catalyst*", Fuel, 2010, vol. 89, pp. 2697-2702.
Xu, Y., et al., "*Methane Activation Without Using Oxidants Over Mo/HZSM-5 Zeolite Catalysts,*" Catalysis Letters, 1995, vol. 30, pp. 135-149.

*Primary Examiner* — Thuan D Dang

(57) ABSTRACT

Disclosed is a process for the conversion of acyclic C$_5$ feedstock to a product comprising cyclic C$_5$ compounds, including cyclopentadiene, and catalyst compositions for use in such process. The process comprises contacting the feedstock and, optionally, hydrogen under acyclic C$_5$ conversion conditions in the presence of a catalyst composition to form said product. The catalyst composition comprises a microporous crystalline metallosilicate, a Group 10 metal or compound thereof, and a Group 11 metal or compound thereof.

18 Claims, 10 Drawing Sheets

PRODUCTION OF CYCLIC $C_5$ COMPOUNDS

CROSS-REFERENCE TO RELATED APPLICATIONS

This invention claims priority to and the benefit of U.S. Ser. No. 62/250,689, filed Nov. 4, 2015. This application relates to U.S. Ser. No. 62/250,675, filed Nov. 4, 2015; U.S. Ser. No. 62/250,681, filed Nov. 4, 2015; and U.S. Ser. No. 62/250,688, filed Nov. 4, 2015.

FIELD OF THE INVENTION

This invention relates to a process for producing cyclic $C_5$ compounds, especially cyclopentadiene, from acyclic feedstocks, and catalyst compositions for use in such a process.

BACKGROUND OF THE INVENTION

Cyclopentadiene (CPD) and its dimer dicyclopentadiene (DCPD) are highly desired raw materials used throughout the chemical industry in a wide range of products such as polymeric materials, polyester resins, synthetic rubbers, solvents, fuels, fuel additives, etc. In addition, cyclopentane and cyclopentene are useful as solvents, and cyclopentene may be used as a monomer to produce polymers and as a starting material for other high value chemicals.

Cyclopentadiene (CPD) and its dimer dicyclopentadiene (DCPD) are highly desired raw materials used throughout the chemical industry in a wide range of products such as polymeric materials, polyester resins, synthetic rubbers, solvents, fuels, fuel additives, etc. Cyclopentadiene (CPD) is currently a minor byproduct of liquid fed steam cracking (for example, naphtha and heavier feed). As existing and new steam cracking facilities shift to lighter feeds, less CPD is/will be produced while demand for CPD is rising. High cost due to supply limitations impacts the potential end product use of CPD in polymers. More CPD-based polymer products and other high value products could be produced if additional CPD could be produced at unconstrained rates and preferably at a cost lower than recovery from steam cracking. Co-production of other cyclic $C_5$ compounds is also desirable. Cyclopentane and cyclopentene can have high value as solvents, while cyclopentene may be used as a co-monomer to produce polymers and as a starting material for other high value chemicals.

In particular, it would be advantageous to develop a catalytic process for producing cyclic $C_5$ compounds, including CPD as the primary product, from plentiful $C_5$ feedstocks while minimizing production of light ($C_{4-}$) byproducts. While lower hydrogen content feedstocks (for example, cyclic, alkenes, dialkenes) could be preferred because the reaction endotherm is reduced and thermodynamic constraints on conversion are improved, non-saturates are more expensive than saturated feedstocks. Linear $C_5$ skeletal structure is preferred over branched $C_5$ skeletal structures due to both reaction chemistry and the lower value of linear $C_5$ relative to branched $C_5$ (due to octane differences). An abundance of $C_5$ hydrocarbon feedstocks is available from unconventional gas and shale oil, as well as reduced use in motor fuels due to stringent fuel regulations. $C_5$ feedstocks may also be derived from bio-feeds.

Various catalytic dehydrogenation technologies are currently used to produce mono and diolefins from $C_3$ and $C_4$ alkanes, but not cyclic mono-olefins or cyclic di-olefins. A typical process uses Pt/Sn supported on alumina as the active catalyst. Another useful process uses chromia on alumina. See, B. V. Vora, "Development of Dehydrogenation Catalysts and Processes," Topics in Catalysis, vol. 55, pp. 1297-1308, 2012; and J. C. Bricker, "Advanced Catalytic Dehydrogenation Technologies for Production of Olefins," Topics in Catalysis, vol. 55, pp. 1309-1314, 2012.

Still another common process uses Pt/Sn supported on Zn and/or Ca aluminate to dehydrogenate propane. While these processes are successful in dehydrogenating alkanes, they do not perform cyclization, which is critical to producing CPD. Pt—Sn/alumina and Pt—Sn/aluminate catalysts exhibit moderate conversion of n-pentane, but such catalysts have poor selectivity and yield to cyclic $C_5$ products.

Pt supported on chlorided alumina catalysts are used to reform low octane naphtha to aromatics such as benzene and toluene. See, U.S. Pat. No. 3,953,368 (Sinfelt), "Polymetallic Cluster Compositions Useful as Hydrocarbon Conversion Catalysts." While these catalysts are effective in dehydrogenating and cyclizing $C_6$ and higher alkanes to form $C_6$ aromatic rings, they are less effective in converting acyclic $C_5$s to cyclic $C_5$s. These Pt supported on chlorided alumina catalysts exhibit low yields of cyclic $C_5$ and exhibit deactivation within the first two hours of time on stream. Cyclization of $C_6$ and $C_7$ alkanes is aided by the formation of an aromatic ring, which does not occur in $C_5$ cyclization. This effect may be due in part to the much higher heat of formation for CPD, a cyclic $C_5$, as compared to benzene, a cyclic $C_6$, and toluene, a cyclic $C_7$. This is also exhibited by Pt/Ir and Pt/Sn supported on chlorided alumina. Although these alumina catalysts perform both dehydrogenation and cyclization of $C_{6+}$ species to form $C_6$ aromatic rings, a different catalyst will be needed to convert acyclic $C_5$ compounds to cyclic $C_5$ compounds.

Likewise, light paraffins can be converted to aromatics over zeolite catalysts, such as those based on ZSM-5. A study by Kanazirev et al., showed n-pentane is readily converted over $Ga_2O_3$/H-ZSM-5. See Kanazirev et al., "Conversion of $C_8$ aromatics and n-pentane over $Ga_2O_3$/H-ZSM-5 mechanically mixed catalysts," Catalysis Letters, vol. 9, pp. 35-42, 1991. No production of cyclic $C_5$ was reported while upwards of 6 wt % aromatics were produced at 440° C. and 1.8 $hr^{-1}$ WHSV. Mo/ZSM-5 catalysts have also been shown to dehydrogenate and/or cyclize paraffins, especially methane. See, Y. Xu, S. Liu, X. Guo, L. Wang, and M. Xie, "Methane activation without using oxidants over Mo/HZSM-5 zeolite catalysts," Catalysis Letters, vol. 30, pp. 135-149, 1994. High conversion of n-pentane using Mo/ZSM-5 was demonstrated with no production of cyclic $C_5$ and high yield to cracking products. This shows that ZSM-5-based catalysts can convert paraffins to a $C_6$ ring, but not necessarily to produce a $C_5$ ring.

U.S. Pat. No. 5,254,787 discloses catalytic dehydrogenation and/or dehydrocyclization of $C_{2+}$ alkanes over a Group VIA or Group VIII metal-containing non-acidic zeolite having the structure of NU-87. A distinction is drawn between $C_{2-5}$ and $C_{6+}$ alkanes, with dehydrogenation of $C_{2-5}$ alkanes producing linear or branched mono- or di-olefins whereas dehydrogenation of $C_{6+}$ alkanes yields aromatics. Similar chemistry is employed in U.S. Pat. No. 5,192,728, but using a catalyst composition consisting essentially of a dehydrogenation metal and a non-acidic microporous crystalline material containing tin.

U.S. Pat. No. 5,284,986 discloses a dual-stage process for the production of cyclopentane and cyclopentene from n-pentane, preferably without interstage processing of the first-stage product mixture. The first stage involves dehydrogenation and dehydrocyclization of n-pentane to a mixture of paraffins, mono- and di-olefins, and naphthenes over a catalyst comprising a Group VIA or Group VIII metal and a non-acidic microporous material, such as ZSM-5. This mixture is then introduced to a second-stage reactor where dienes, especially cyclopentadiene, are converted to olefins and saturates over a second catalyst comprising palladium and a non-acidic microporous material, again such as ZSM-5. In the only Example, which uses Pt/Sn-ZSM-5 as the first stage catalyst and Pd/Sn-ZSM-5 as the second stage catalyst, no cyclopentadiene was detected in the second-stage reactor effluent.

U.S. Pat. No. 2,438,398; U.S. Pat. No. 2,438,399; U.S. Pat. No. 2,438,400; U.S. Pat. No. 2,438,401; U.S. Pat. No. 2,438,402; U.S. Pat. No. 2,438,403; and U.S. Pat. No. 2,438,404 (Kennedy) disclosed production of CPD from 1,3-pentadiene over various catalysts. Low operating pressures, low per pass conversion, and low selectivity make this process undesirable. Additionally, 1,3-pentadiene is not a readily available feedstock, unlike n-pentane. See also, Kennedy et al., "Formation of Cyclopentadiene from 1,3-Pentadiene," Industrial & Engineering Chemistry, vol. 42, pp. 547-552, 1950.

Fel'dblyum et al., in "Cyclization and dehydrocyclization of $C_5$ hydrocarbons over platinum nanocatalysts and in the presence of hydrogen sulfide," *Doklady Chemistry*, vol. 424, pp. 27-30, 200, reported production of CPD from 1,3-pentadiene, n-pentene, and n-pentane. Yields to CPD were as high as 53%, 35%, and 21% for the conversion of 1,3-pentadiene, n-pentene, and n-pentane respectively at 600° C. on 2% $Pt/SiO_2$. While initial production of CPD was observed, drastic catalyst deactivation within the first minutes of the reaction was observed. Experiments conducted on Pt-containing silica show moderate conversion of n-pentane over Pt—$Sn/SiO_2$, but with poor selectivity and yield to cyclic $C_5$ products. The use of $H_2S$ as a 1,3-pentadiene cyclization promoter was presented by Fel'dblyum, infra, as well as in Marcinkowski, "Isomerization and Dehydrogenation of 1,3-Pentadiene," M.S., University of Central Florida, 1977. Marcinkowski showed 80% conversion of 1,3,-pentadiene with 80% selectivity to CPD with $H_2S$ at 700° C. High temperature, limited feedstock, and potential of products containing sulfur that would later need scrubbing make this process undesirable.

López et al., in "n-Pentane Hydroisomerization on Pt Containing HZSM-5, HBEA and SAPO-11," *Catalysis Letters*, vol. 122, pp. 267-273, 2008, studied reactions of n-pentane on Pt-containing zeolites, including H-ZSM-5. At intermediate temperatures (250° C.-400° C.), they reported efficient hydroisomerization of n-pentane on the Pt-zeolites with no discussion of cyclopentenes formation. It is desirable to avoid this deleterious chemistry as branched $C_5$ do not produce cyclic $C_5$ as efficiently as linear $C_5$, as discussed above.

Li et al., in "Catalytic dehydroisomerization of n-alkanes to isoalkenes," *Journal of Catalysis*, vol. 255, pp. 134-137, 2008, also studied n-pentane dehydrogenation on Pt-containing zeolites in which Al had been isomorphically substituted with Fe. These Pt/[Fe]ZSM-5 catalysts were efficient dehydrogenating and isomerizing n-pentane, but under the reaction conditions used, no cyclic $C_5$ were produced and undesirable skeletal isomerization occurred.

U.S. Pat. No. 5,633,421 discloses a process for dehydrogenating $C_2$-$C_5$ paraffins to obtain corresponding olefins. Similarly, U.S. Pat. No. 2,982,798 discloses a process for dehydrogenating an aliphatic hydrocarbon containing 3 to 6, inclusive, carbon atoms. However, neither U.S. Pat. No. 5,633,421, nor U.S. Pat. No. 2,982,798, disclose production of CPD from acyclic $C_5$ hydrocarbons, which are desirable as feedstock because they are plentiful and low cost.

Further, many challenges exist in designing an on-purpose CPD production process. For example, the reaction converting $C_5$ hydrocarbons to CPD is extremely endothermic and is favored by low pressure and high temperature but significant cracking of n-pentane and other $C_5$ hydrocarbons can occur at relatively low temperature (e.g., 450° C.-500° C.). Further challenges include loss of catalyst activity due to coking during the process and further processing needed to remove coke from the catalyst, and the inability to use oxygen-containing gas to directly provide heat input to the reactor without damaging the catalyst.

Hence, there remains a need for a process to convert acyclic $C_5$ feedstock to non-aromatic, cyclic $C_5$ hydrocarbon, namely cyclopentadiene, preferably at commercial rates and conditions. Further, there is a need for a catalytic process targeted for the production of cyclopentadiene which generates cyclopentadiene in high yield from plentiful $C_5$ feedstocks without excessive production of $C_{4-}$ cracked products and with acceptable catalyst aging properties. Additionally, there is a need for processes and systems for on-purpose CPD production from acyclic $C_5$ hydrocarbons, which address the above-described challenges.

SUMMARY OF THE INVENTION

According to the present invention, it has now been found that acyclic $C_5$ hydrocarbons, including n-pentane, can be converted to cyclic $C_5$ compounds, including cyclopentadiene, in high yield over a catalyst comprising a microporous crystalline metallosilicate, a Group 10 metal, especially platinum, and a Group 11 metal, especially silver and/or copper. Loss of $C_5$ feed to $C_{4-}$ by-products is generally low and catalyst aging is significantly less severe than with prior art catalysts.

Thus, the invention resides in one aspect in a process for producing cyclic $C_5$ compounds, including cyclopentadiene, the process comprising:
(a) contacting a feed containing acyclic $C_5$ hydrocarbons with a catalyst comprising (i) a microporous crystalline metallosilicate having a constraint index less than or equal to 12, such as from 1 to 12, (ii) a Group 10 metal or a compound thereof, and (iii) a Group 11 metal or a compound thereof under conditions effective to convert at least part of the acyclic $C_5$ hydrocarbons in the feed to produce an effluent comprising cyclopentadiene; and (b) recovering cyclopentadiene from the effluent.

In another aspect, the invention resides in a process for producing cyclic $C_5$ compounds, including cyclopentadiene, the process comprising:
(a) contacting a feed containing acyclic $C_5$ hydrocarbons with a catalyst comprising (i) a microporous crystalline metallosilicate having a constraint index less than or equal to 12, such as from 1 to 12, (ii) platinum or a compound thereof, and (iii) silver or a compound thereof under conditions effective to convert at least part of the acyclic $C_5$ hydrocarbons in the feed to produce an effluent comprising cyclopentadiene; and
(b) recovering cyclopentadiene from the effluent.

In yet another aspect, the invention resides in a process for producing cyclic $C_5$ compounds, including cyclopentadiene, the process comprising:
(a) contacting a feed containing acyclic $C_5$ hydrocarbons with a catalyst comprising (i) a microporous crystalline metallosilicate having a constraint index less than or equal to 12, such as from 1 to 12, (ii) platinum or a compound thereof, and (iii) copper or a compound thereof under conditions effective to convert at least part of the acyclic $C_5$ hydrocarbons in the feed to produce an effluent comprising cyclopentadiene; and (b) recovering cyclopentadiene from the effluent.

In a further aspect, the invention resides in catalyst composition for the conversion of an acyclic $C_5$ feedstock to a product comprising cyclic $C_5$ compounds including cyclopentadiene, said catalyst composition comprising a microporous crystalline metallosilicates (such as a crystalline aluminosilicate), at least 0.005 wt % of platinum, based on the weight of the catalyst composition, and one or more Group 11 metals or compounds thereof selected from silver and/or copper, said crystalline metallosilicate having a $SiO_2/M$ molar ratio (where M is a group 8, 11, or 13 metal) in the range from about 2 to about 2000 and being selected from the group consisting of MWW, MFI, LTL, MOR, BEA, TON, MTW, MTT, FER, MRE, MFS, MEL, DDR, EUO, and FAU and mixtures thereof.

DETAILED DESCRIPTION OF THE EMBODIMENTS

Definitions

Figure 1A:
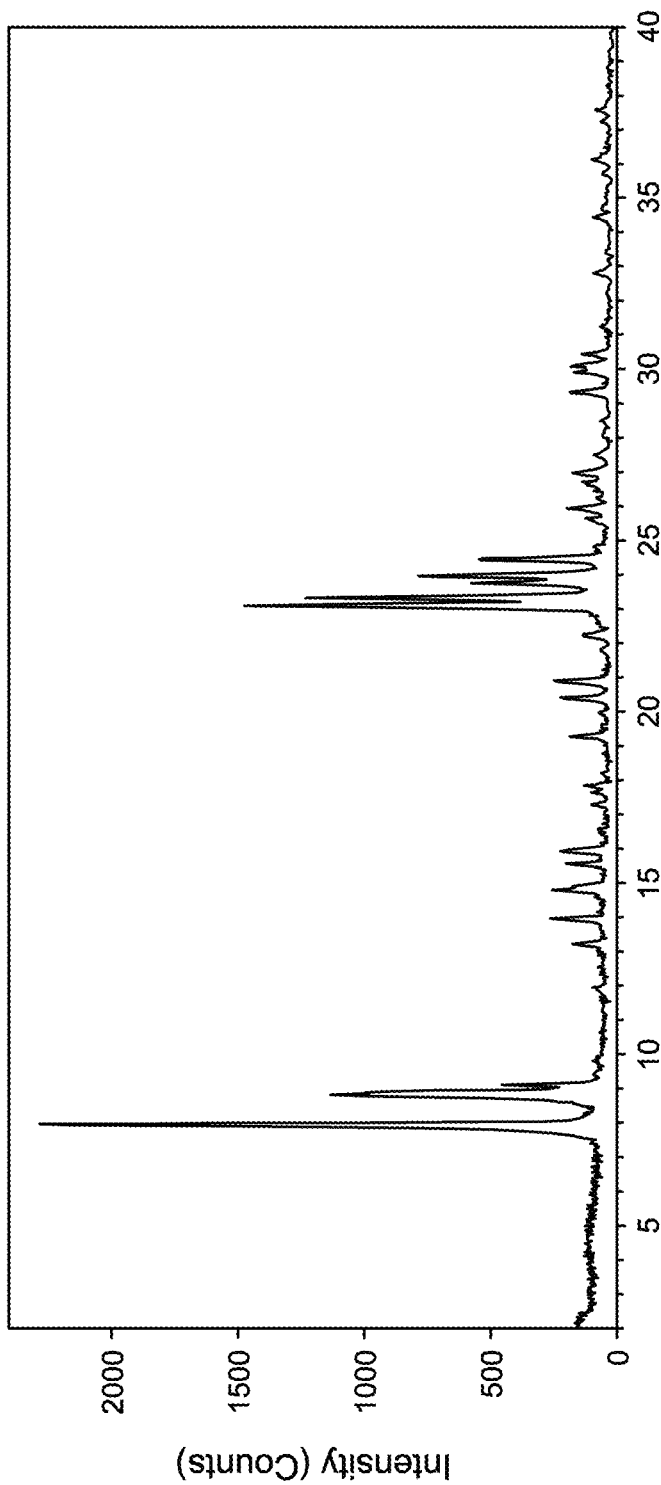
FIG. 1A shows an X-ray diffraction (XRD) pattern of the as-synthesized ZSM-5 produced in Comparative Example 1.

For the purpose of this specification and appended claims, the following terms are defined.

The term "saturates" includes, but is not limited to, alkanes and cycloalkanes.

The term "non-saturates" includes, but is not limited to, alkenes, dialkenes, alkynes, cyclo-alkenes, and cyclo-dialkenes.

The term "cyclics $C_5$" or "$cC_5$" includes, but is not limited to, cyclopentane, cyclopentene, cyclopentadiene, and mixtures of two or more thereof. The term "cyclic $C_5$" or "$cC_5$" also includes alkylated analogs of any of the foregoing, e.g., methyl cyclopentane, methyl cyclopentene, and methyl cyclopentadiene. It should be recognized for purposes of the invention that cyclopentadiene spontaneously dimerizes over time to form dicyclopentadiene via Diels-Alder condensation over a range of conditions, including ambient temperature and pressure.

The term "acyclics" includes, but is not limited to, linear and branched saturates and non-saturates.

The term "aromatic" means a planar cyclic hydrocarbyl with conjugated double bonds, such as benzene. As used herein, the term aromatic encompasses compounds containing one or more aromatic rings, including, but not limited to, benzene, toluene, and xylene and polynuclear aromatics (PNAs), which include naphthalene, anthracene, chrysene, and their alkylated versions. The term "$C_{6+}$ aromatics" includes compounds based upon an aromatic ring having six or more ring atoms, including, but not limited to, benzene, toluene, and xylene and polynuclear aromatics (PNAs), which include naphthalene, anthracene, chrysene, and their alkylated versions.

The term "BTX" includes, but is not limited to, a mixture of benzene, toluene, and xylene (ortho and/or meta and/or para).

The term "coke" includes, but is not limited to, a low hydrogen content hydrocarbon that is adsorbed on the catalyst composition.

The term "$C_n$" means hydrocarbon(s) having n carbon atom(s) per molecule, wherein n is a positive integer.

The term "$C_{n+}$" means hydrocarbon(s) having at least n carbon atom(s) per molecule.

The term "$C_{n-}$" means hydrocarbon(s) having no more than n carbon atom(s) per molecule.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

The term "$C_5$ feedstock" includes a feed stock containing n-pentane, such as a feedstock which is predominately normal pentane and isopentane (also referred to as methylbutane), with smaller fractions of cyclopentane and neopentane (also referred to as 2,2-dimethylpropane).

All numbers and references to the Periodic Table of Elements are based on the new notation as set out in Chemical and Engineering News, 63(5), 27 (1985), unless otherwise specified.

The term "Group 1 alkali metal" means an element in Group 1 of the Periodic Table and includes, but is not limited to, Li, Na, K, Rb, Cs, and a mixture of two or more thereof, and excludes hydrogen.

The term "Group 2 alkaline earth metal" means an element in Group 2 of the Periodic Table and includes, but is not limited to, Be, Mg, Ca, Sr, Ba, and a mixture of two or more thereof.

The term "oxygen" includes $O_2$, $H_2O$, CO, and $CO_2$.

The term "Group 10 metal" means an element in Group 10 of the Periodic Table and includes Ni, Pd, and Pt.

The term "Group 11 metal" means an element in Group 11 of the Periodic Table and includes Cu, Ag, and Au.

The term "constraint index" is defined in U.S. Pat. No. 3,972,832 and U.S. Pat. No. 4,016,218, both of which are incorporated herein by reference.

As used herein, the term "molecular sieve of the MCM-22 family" (or "material of the MCM-22 family" or "MCM-22 family material" or "MCM-22 family zeolite") includes one or more of:

molecular sieves made from a common first degree crystalline building block unit cell, which unit cell has the MWW framework topology (A unit cell is a spatial arrangement of atoms, which if tiled in three-dimensional space describes the crystal structure. Such crystal structures are discussed in the "Atlas of Zeolite Framework Types," Fifth edition, 2001, the entire content of which is incorporated as reference.);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks may be in a regular fashion, an irregular fashion, a random fashion, or any combination thereof; and molecular sieves made by any regular or random 2-dimensional or 3-dimensional combination of unit cells having the MWW framework topology.

The MCM-22 family includes those molecular sieves having an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as incident radiation and a diffractometer equipped with a scintillation counter and associated computer as the collection system.

As used herein, the term "molecular sieve" is used synonymously with the term "microporous crystalline metallosilicate."

As used herein, the term "carbon selectivity" means the moles of carbon in the respective cyclic $C_5$, CPD, $C_1$, and $C_{2-4}$ formed divided by total moles of carbon in the pentane converted. The phrase "a carbon selectivity to cyclic $C_5$ of at least 30%" means that 30 moles of carbon in the cyclic $C_5$ is formed per 100 moles of carbon in the pentane converted.

As used herein, the term "conversion" means the moles of carbon in the acyclic $C_5$ feedstock that is converted to a product. The phrase "a conversion of at least 70% of said acyclic $C_5$ feedstock to said product" means that at least 70% of the moles of said acyclic $C_5$ feedstock was converted to a product.

As used herein, the term "reactor system" refers to a system including one or more reactors and all optional equipment used in the production of cyclopentadiene.

As used herein, the term "reactor" refers to any vessel(s) in which a chemical reaction occurs. Reactor includes both distinct reactors as well as reaction zones within a single reactor apparatus and as applicable, reactions zones across multiple reactors. For example, a single reactor may have multiple reaction zones. Where the description refers to a first and second reactor, the person of ordinary skill in the art will readily recognize such reference includes two reactors as well as a single reactor vessel having first and second reaction zones. Likewise, a first reactor effluent and a second reactor effluent will be recognized to include the effluent from the first reaction zone and the second reaction zone of a single reactor, respectively.

A reactor/reaction zone may be an adiabatic reactor/reaction zone or adiabatic reactor/reaction zone. As used herein, the term "adiabatic" refers to a reaction zone for which there is essentially no heat input into the system other than by a flowing process fluid. A reaction zone that has unavoidable losses due to conduction and/or radiation may also be considered adiabatic for the purpose of this invention As used herein, the term "diabatic" refers to a reactor/reaction zone to which heat is supplied by a means in addition to that provided by the flowing process fluid.

As used herein, the term "moving bed" reactor refers to a zone or vessel with contacting of solids (e.g., catalyst particles) and gas flows such that the superficial gas velocity (U) is below the velocity required for dilute-phase pneumatic conveying of solid particles in order to maintain a solids bed with void fraction below 95%. In a moving bed reactor, the solids (e.g., catalyst material) may slowly travel through the reactor and may be removed from the bottom of the reactor and added to the top of the reactor. A moving bed reactor may operate under several flow regimes including settling or moving packed-bed regime ($U<U_{mf}$), bubbling regime ($U_{mf}<U<U_{mb}$), slugging regime ($U_{mb}<U<U_c$), transition to and turbulent fluidization regime ($U_c<U<U_{tr}$), and fast-fluidization regime ($U>U_{tr}$), where Umf is minimum fluidizing velocity, Umb is minimum bubbling velocity, Uc is the velocity at which fluctuation in pressure peaks, and tr is transport velocity. These different fluidization regimes have been described in, for example, Kunii, D., Levenspiel, O., Chapter 3 of *Fluidization Engineering, 2$^{nd}$ Edition*, Butterworth-Heinemann, Boston, 1991 and Walas, S. M., Chapter 6 of *Chemical Process Equipment, Revised 2$^{nd}$ Edition*, Butterworth-Heinemann, Boston, 2010, which are incorporated by reference.

As used herein, the term "settling bed" reactor refers to a zone or vessel wherein particulates contact with gas flows such that the superficial gas velocity (U) is below the minimum velocity required to fluidize the solid particles (e.g., catalyst particles), the minimum fluidization velocity ($U_{mf}$), $U<U_{mf}$ in at least a portion of the reaction zone, and/or operating at a velocity higher than the minimum fluidization velocity while maintaining a gradient in gas and/or solid property (such as, temperature, gas or solid composition, etc.) axially up the reactor bed by using reactor internals to minimize gas-solid back-mixing. Description of the minimum fluidization velocity is given in, for example, Kunii, D., Levenspiel, O., Chapter 3 of *Fluidization Engineering, 2$^{nd}$ Edition*, Butterworth-Heinemann, Boston, 1991 and Walas, S. M., Chapter 6 of *Chemical Process Equipment, Revised 2$^{nd}$ Edition*, Butterworth-Heinemann, Boston, 2010. A settling bed reactor may be a "circulating settling bed reactor," which refers to a settling bed with a movement of solids (e.g., catalyst material) through the reactor and at least a partial recirculation of the solids (e.g., catalyst material). For example, the solids (e.g., catalyst material) may have been removed from the reactor, regenerated, reheated, and/or separated from the product stream and then returned back to the reactor.

As used herein, the term "fluidized bed" reactor refers to a zone or vessel with contacting of solids (e.g., catalyst particles) and gas flows such that the superficial gas velocity (U) is sufficient to fluidize solid particles (i.e., above the minimum fluidization velocity $U_{mf}$) and is below the velocity required for dilute-phase pneumatic conveying of solid particles in order to maintain a solids bed with void fraction below 95%. As used herein the term "cascaded fluid-beds" means a series arrangement of individual fluid-beds such that there can be a gradient in gas and/or solid property (such as, temperature, gas or solid composition, pressure, etc.) as the solid or gas cascades from one fluid-bed to another. Locus of minimum fluidization velocity is given in, for example, Kunii, D., Levenspiel, O., Chapter 3 of *Fluidization Engineering*, 2$^{nd}$ Edition, Butterworth-Heinemann, Boston, 1991 and Walas, S. M., Chapter 6 of *Chemical Process Equipment*, Revised 2$^{nd}$ Edition, Butterworth-Heinemann, Boston, 2010. A fluidized bed reactor may be a moving fluidized bed reactor, such as a "circulating fluidized bed reactor," which refers to a fluidized bed with a movement of solids (e.g., catalyst material) through the reactor and at least a partial recirculation of the solids (e.g., catalyst material). For example, the solids (e.g., catalyst material) may have been removed from the reactor, regenerated, reheated and/or separated from the product stream and then returned back to the reactor.

As used herein the term "riser" reactor (also known as a transport reactor) refers to a zone or vessel (such as, vertical cylindrical pipe) used for net upwards transport of solids (e.g., catalyst particles) in fast-fluidization or pneumatic conveying fluidization regimes. Fast fluidization and pneumatic conveying fluidization regimes are characterized by superficial gas velocities (U) greater than the transport velocity ($U_{tr}$). Fast fluidization and pneumatic conveying fluidization regimes are also described in Kunii, D., Levenspiel, O., Chapter 3 of *Fluidization Engineering*, 2$^{nd}$ Edition, Butterworth-Heinemann, Boston, 1991 and Walas, S. M., Chapter 6 of *Chemical Process Equipment*, Revised 2$^{nd}$ Edition, Butterworth-Heinemann, Boston, 2010. A fluidized bed reactor, such as a circulating fluidized bed reactor, may be operated as a riser reactor.

As used herein, the term "fired tubes" reactor refers to a furnace and parallel reactor tube(s) positioned within a radiant section of the furnace. The reactor tubes contain a catalytic material (e.g., catalyst particles), which contacts reactant(s) to form a product.

As used herein, the term "convectively heated tubes" reactor refers to a conversion system comprising parallel reactor tube(s) containing a catalytic material and positioned within an enclosure. While any known reactor tube configuration or enclosure may be used, preferably the conversion system comprises multiple parallel reactor tubes within a convective heat transfer enclosure. Preferably, the reactor tubes are straight rather than having a coiled or curved path through the enclosure (athough coiled or curved tubes may be used). Additionally, the tubes may have a cross section that is circular, elliptical, rectangular, and/or other known shapes. The tubes are preferentially heated with a turbine exhaust stream produced by a turbine burning fuel gas with a compressed gas comprising oxygen. In other aspects, the reactor tubes are heated by convection with hot gas produced by combustion in a furnace, boiler, or excess air burner. However, heating the reactor tubes with turbine exhaust is preferred because of the co-production of shaft power among other advantages.

As used herein, the term "fixed bed" or "packed bed" reactor refers to a zone or vessel (such as, vertical or horizontal, cylindrical pipe or a spherical vessel) and may include transverse (also known as cross flow), axial flow and/or radial flow of the gas, where solids (e.g., catalyst particles) are substantially immobilized within the reactor and gas flows such that the superficial velocity (U) is below the velocity required to fluidize the solid particles (i.e., below the minimum fluidization velocity $U_{mf}$) and/or the gas is moving in a downward direction so that solid particle fluidization is not possible.

As used herein, the term "cyclical" refers to a periodic recurring or repeating event that occurs according to a cycle. For example, reactors (e.g., cyclic fixed bed) may be cyclically operated to have a reaction interval, a reheat interval and/or a regeneration interval. The duration and/or order of the interval steps may change over time.

As used herein, the term "co-current" refers to a flow of two streams (e.g., stream (a), stream (b)) in substantially the same direction. For example, if stream (a) flows from a top portion to a bottom portion of at least one reaction zone and stream (b) flows from a top portion to a bottom portion of at least one reaction zone, the flow of stream (a) would be considered co-current to the flow of stream (b). On a smaller scale within the reaction zone, there may be regions where flow may not be co-current.

As used herein, the term "counter-current" refers to a flow of two streams (e.g., stream (a), stream (b)) in substantially opposing directions. For example, if stream (a) flows from a top portion to a bottom portion of the at least one reaction zone and stream (b) flows from a bottom portion to a top portion of the at least one reaction zone, the flow of stream (a) would be considered counter-current to the flow of stream (b). On a smaller scale within the reaction zone, there may be regions where flow may not be counter-current.

Feedstock

An acyclic $C_5$ feedstock useful herein is obtainable from crude oil or natural gas condensate, and can include cracked $C_5$ hydrocarbons (in various degrees of unsaturation: alkenes, dialkenes, alkynes) produced by refining and chemical processes, such as fluid catalytic cracking (FCC), reforming, hydrocracking, hydrotreating, coking, and steam cracking.

In one or more embodiments, the acyclic $C_5$ feedstock useful in the present process comprises pentane, pentene, pentadiene, and mixtures of two or more thereof. Preferably, in one or more embodiments, the acyclic $C_5$ feedstock comprises at least about 50 wt %, or 60 wt %, or 75 wt %, or 90 wt % n-pentane, or in the range from about 50 wt % to about 100 wt % n-pentane.

The acyclic $C_5$ feedstock used herein, optionally, does not comprise $C_{6+}$ aromatic compounds, such as benzene, toluene, or xylene (ortho, meta or para). In some embodiments, the feedstock comprises less than 5 wt %, preferably less than 1 wt %, preferably less than 0.01 wt %, preferably 0 wt %, $C_{6+}$ aromatic compounds.

The acyclic $C_5$ feedstock used herein, optionally, does not comprise $C_{4-}$ compounds. In some embodiments, the feedstock comprises less than 5 wt %, preferably less than 1 wt %, preferably less than 0.01 wt %, preferably 0 wt %, $C_{4-}$ compounds.

The acyclic $C_5$ feedstock used herein, optionally, does not comprise $C_{4-}$ compounds and $C_{6+}$ aromatic compounds. In some embodiments, the feedstock comprises less than 5 wt %, preferably less than 1 wt %, preferably less than 0.01 wt %, preferably at 0 wt %, of both $C_{4-}$ and $C_{6+}$ aromatic compounds.

Alternately, the $C_5$ feedstock is substantially free of oxygen-containing compounds. "Substantially free" used in this context means the feedstock comprises less than about 1.0 wt %, based upon the weight of the feed, e.g., less than about 0.1 wt %, less than about 0.01 wt %, less than about 0.001 wt %, less than about 0.0001 wt %, less than about 0.00001 wt % oxygen-containing compounds.

Acyclic $C_5$ Conversion Process

This invention relates to a process for conversion of an acyclic $C_5$ feedstock to a product comprising cyclic $C_5$ compounds. The process comprises the steps of contacting said feedstock and, optionally, hydrogen under acyclic $C_5$ conversion conditions in the presence of one or more catalyst compositions, including but not limited to the catalyst compositions described herein, to form said product.

In one or more embodiments, the product of the process for conversion of an acyclic $C_5$ feedstock comprises cyclic $C_5$ compounds. The cyclic $C_5$ compounds comprise one or more of cyclopentane, cyclopentene, cyclopentadiene, and includes mixtures thereof. In one or more embodiments, the cyclic $C_5$ compounds comprise at least about 20 wt %, or 30 wt %, or 40 wt %, or 50 wt % cyclopentadiene, or in the range of from about 10 wt % to about 80 wt %, alternately 20 wt % to 70 wt %.

The acyclic $C_5$ conversion process can be conducted in a wide range of reactor configurations including: convectively heated tubes (as described in U.S. Ser. No. 62/250,674 filed Nov. 4, 2015), fired tubes (as described in U.S. Ser. No. 62/250,693 filed Nov. 4, 2015), a riser reactor (as described in U.S. Ser. No. 62/250,682 filed Nov. 4, 2015), a circulating fluidized bed or a circulating settling bed with counter-current flow (as described in U.S. Ser. No. 62/250,680 filed Nov. 4, 2015), and a cyclic fluidized bed reactor or a cyclic fixed bed reactor (as described in U.S. Ser. No. 62/250,677 filed Nov. 4, 2015). In addition, the $C_5$ conversion process can be conducted in a single reaction zone or in a plurality of reaction zones, such as an adiabatic reaction zone followed by a diabatic reaction zone (as described in U.S. Ser. No. 62/250,697 filed Nov. 4, 2015).

Typically, the acyclic $C_5$ hydrocarbon(s) contained in the $C_5$ feedstock is fed into a first reactor loaded with a catalyst, where the acyclic $C_5$ hydrocarbons contact the catalyst under conversion conditions, whereupon at least a portion of the acyclic $C_5$ hydrocarbon(s) molecules are converted into CPD molecules, and a reaction product containing CPD and, optionally, other cyclic hydrocarbons (e.g., $C_5$ cyclic hydrocarbons such as cyclopentane and cyclopentene) exits the first reactor as a first reactor hydrocarbon effluent. Preferably, a hydrogen co-feedstock comprising hydrogen and, optionally, light hydrocarbons, such as $C_1$-$C_4$ hydrocarbons, is also fed into the first reactor (as described in U.S. Ser. No. 62/250,702 filed Nov. 4, 2015). Preferably, at least a portion of the hydrogen co-feedstock is admixed with the $C_5$ feedstock prior to being fed into the first reactor. The presence of hydrogen in the feed mixture at the inlet location, where the feed first comes into contact with the catalyst, prevents or reduces the formation of coke on the catalyst particles.

In the process described herein, an acyclic $C_5$ feedstock as described above, optionally together with hydrogen, is contacted with a catalyst comprising (i) a microporous crystalline metallosilicate having a constraint index of up to 12 (preferably from 1 to 12), (ii) a Group 10 metal or a compound thereof (preferably Pt), and (iii) one or more Group 11 metals (preferably Ag and/or Cu) or a compound thereof under conditions effective to convert at least part of the acyclic $C_5$ hydrocarbons in the feedstock to produce an effluent comprising one or more cyclic $C_5$ compounds. The cyclic $C_5$ compounds may comprise one or more of cyclopentane, cyclopentene, cyclopentadiene, and includes mixtures thereof. In one or more embodiments, the cyclic $C_5$ compounds in the effluent comprise at least about 20 wt %, or 30 wt %, or 40 wt %, or 50 wt % cyclopentadiene, or in the range of from about 10 wt % to about 80 wt %, alternately 20 wt % to 70 wt %, cyclopentadiene. Cyclopentadiene can then be recovered from the effluent. Other cyclic $C_5$ compounds, such as cyclopentane and/or cyclopentene, can also be recovered or can be recycled to the conversion process together with some or all of the unreacted acyclic $C_5$ components.

In one or more embodiments, the acyclic $C_5$ conversion conditions include at least a temperature, a partial pressure, a weight hourly space velocity (WHSV). The temperature is in the range of about 400° C. to about 700° C., or in the range from about 450° C. to about 650° C., preferably, in the range from about 500° C. to about 600° C. The partial pressure in the range of about 3 to about 100 psia at the reactor inlet (21 kPa-a to 690 kPa-a), or in the range from about 3 to about 50 psia (21 to 345 kPa-a), preferably, in the range from about 3 psia to about 20 psia (21 to 138 kPa-a). The weight hourly space velocity in the range from about 1 to about 50 $hr^{-1}$, or in the range from about 1 to about 20 $hr^{-1}$. Such conditions include a molar ratio of the optional hydrogen co-feed to the acyclic $C_5$ feedstock in the range of about 0 to 3 (e.g., 0.01 to 3.0), or in the range from about 1 to about 2. Such conditions may also include co-feed $C_1$-$C_4$ hydrocarbons with the acyclic $C_5$ feed.

In one or more embodiments, this invention relates to a process for conversion of n-pentane to cyclopentadiene comprising the steps of contacting n-pentane and, optionally, hydrogen (if present, typically H is present at a ratio to n-pentane of 0.01 to 3.0) with any one of the catalyst compositions of this invention to form cyclopentadiene at a temperature of 400° C. to 650° C., a partial pressure of 3 to about 100 psia at the reactor inlet (21 kPa-a to 690 kPa-a), and a weight hourly space velocity of 1 to about 50 $hr^{-1}$.

In the presence of the catalyst, a number of desired and undesirable side reactions may take place. The net effect of the reactions is the production of hydrogen and the increase of total volume (assuming constant total pressure). One particularly desired overall reaction (i.e., intermediate reaction steps are not shown) is:

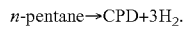
$n$-pentane→CPD+3H$_2$.

Additional overall reactions include, but are not limited to:

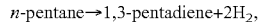
$n$-pentane→1,3-pentadiene+2H$_2$,

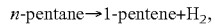
$n$-pentane→1-pentene+H$_2$,

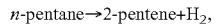
$n$-pentane→2-pentene+H$_2$,

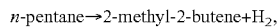
$n$-pentane→2-methyl-2-butene+H$_2$,

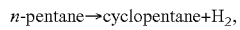
$n$-pentane→cyclopentane+H$_2$,

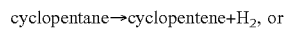
cyclopentane→cyclopentene+H$_2$, or

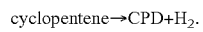
cyclopentene→CPD+H$_2$.

Fluids inside the first reactor are essentially in gas phase. At the outlet of the first reactor, a first reactor hydrocarbon effluent, preferably in gas phase, is obtained. The first reactor hydrocarbon effluent may comprise a mixture of the following hydrocarbons, among others: heavy components comprising more than 8 carbon atoms such as multiple-ring aromatics; $C_8$, $C_7$, and $C_6$ hydrocarbons such as one-ring aromatics; CPD (the desired product); unreacted $C_5$ feedstock material such as n-pentane; $C_5$ by-products such as pentenes (1-pentene, 2-pentene, e.g.), pentadienes (1,3-pentadiene; 1,4-pentadiene, e.g.), cyclopentane, cyclopentene, 2-methylbutane, 2-methyl-1-butene, 3-methyl-1-butene, 2-methyl-1,3-butadiene, 2,2-dimethylpropane, and the like;

C4 by-products such as butane, 1-butene, 2-butene, 1,3-butadiene, 2-methylpropane; 2-methyl-1-propene, and the like; $C_3$ by-products such as propane, propene, and the like; and $C_2$ by-products such as ethane and ethene; methane; and hydrogen.

The first reactor hydrocarbon effluent may comprise CPD at a concentration of C(CPD)1 wt %, based on the total weight of the $C_5$ hydrocarbons in the first reactor hydrocarbon effluent; and a1≤C(CPD)1≤a2, where a1 and a2 can be, independently, 15, 16, 18, 20, 22, 24, 25, 26, 28, 30, 32, 34, 35, 36, 38, 40, 45, 50, 55, 60, 65, 70, 75, 80 or 85 as long as a1<a2.

The first reactor hydrocarbon effluent may comprise acyclic diolefins at a total concentration of C(ADO)1 wt %, based on the total weight of the $C_5$ hydrocarbons in the first reactor hydrocarbon effluent; and b1≤C(ADO)1≤b2, where b1 and b2 can be, independently, 20, 18, 16, 15, 14, 12, 10, 8, 6, 5, 4, 3, 2, 1, or 0.5, as long as b1<b2. Preferably, 0.5≤C(ADO)≤10.

As a result of the use of the catalyst and the choice of reaction conditions in the first reactor, a high CPD to acyclic diolefin molar ratio in the first reactor hydrocarbon effluent can be achieved such that C(CPD)1/C(ADO)1≥1.5, preferably 1.6, 1.8, 2.0, 2.2, 2.4, 2.5, 2.6, 2.8, 3.0, 3.2, 3.4, 3.5, 3.6, 3.8, 4.0, 5.0, 6.0, 8.0, 10, 12, 14, 15, 16, 18, or 20. The high ratio of C(CPD)1/C(ADO)1 significantly reduces CPD loss as a result of Diels-Alder reactions between CPD and acyclic dienes in subsequent processing steps, and therefore, allows the processes of the present invention to achieve high DCPD yield and high DCPD purity for the subsequently produced DCPD fractions.

Desirably, the total absolute pressure and temperature of the first reactor hydrocarbon effluent should be maintained at levels such that the dimerization of CPD to form DCPD is substantially avoided, and the Diels-Alder reactions between CPD and acyclic dienes are substantially inhibited.

Because the overall conversion from acyclic $C_5$ hydrocarbons to CPD and hydrogen results in substantial volume increase (assuming constant total system pressure), a low partial pressure of CPD and/or a low partial pressure of hydrogen in the reaction mixture favors the conversion of acyclic $C_5$ hydrocarbons. The total partial pressure of $C_5$ hydrocarbons and hydrogen in the first reactor effluent at the outlet is desired to be lower than atmospheric pressure. Thus, where insufficient co-feedstock of a $C_1$-$C_4$ hydrocarbon or other co-feedstock is introduced into the first reactor, the total overall pressure of the first reactor effluent is desirably sub-atmospheric, in order to achieve a level of satisfactory conversion from acyclic $C_5$ hydrocarbons to CPD. However, direct separation of a sub-atmospheric stream has the disadvantage of potential oxygen/air ingress into the system, resulting in oxidation of CPD and other hydrocarbons and formation of undesirable species in the system. Thus, it is desirable that the first reactor hydrocarbon effluent is processed to a higher total pressure before separation thereof. Eductor systems, can be used for that purpose (as described in U.S. Ser. No. 62/250,708 filed Nov. 4, 2015).

Catalyst Composition

The catalyst composition employed in the present process comprises a microporous crystalline metallosilicate, typically an aluminosilicate, a Group 10 metal or compound thereof, and a Group 11 metal, or compound thereof. At least part of the Group 11 metal can be part of the framework metal of the metallosilicate.

Catalyst compositions useful herein include microporous crystalline metallosilicates, such as crystalline aluminosilicates, crystalline ferrosilicates, or other metal containing crystalline silicates (such as those where the metal or metal containing compound is dispersed within the crystalline silicate structure and may or may not be a part of the crystalline framework). Microporous crystalline metallosilicate framework types useful as catalyst compositions herein include, but are not limited to, MWW, MFI, LTL, MOR, BEA, TON, MTW, MTT, FER, MRE, MFS, MEL, DDR, EUO, and FAU.

Particularly suitable microporous metallosilicates for use herein include those of framework type MWW, MFI, LTL, MOR, BEA, TON, MTW, MTT, FER, MRE, MFS, MEL, DDR, EUO, and FAU (such as zeolite beta, mordenite, faujasite, Zeolite L, ZSM-5, ZSM-11, ZSM-22, ZSM-23, ZSM-35, ZSM-48, ZSM-50, ZSM-57, ZSM-58, and MCM-22 family materials) where one or more metals from Groups 8, 11, and 13 of the Periodic Table of the Elements (preferably one or more of Fe, Cu, Ag, Au, B, Al, Ga, and or In) are incorporated in the crystal structure during synthesis or impregnated post crystallization. It is recognized that a metallosilicate may have one or more metals present and, for example, a material may be referred to as a ferrosilicate, but it will most likely still contain small amounts of aluminum.

The microporous crystalline metallosilicates preferably have a constraint index of less than or equal to 12, alternately from 1 to 12, alternately from 2 to 12, alternately from 3 to 12. Aluminosilicates useful herein have a constraint index of less than 12, such as 1 to 12, alternately 3 to 12, and include, but are not limited to Zeolite beta, mordenite, faujasite, Zeolite L, ZSM-5, ZSM-11, ZSM-22, ZSM-23, ZSM-35, ZSM-48, ZSM-50, ZSM-57, ZSM-58, MCM-22 family materials, and mixtures of two or more thereof. In a preferred embodiment, the crystalline aluminosilicate has a constraint index of about 3 to about 12 and is ZSM-5.

ZSM-5 is described in U.S. Pat. No. 3,702,886. ZSM-11 is described in U.S. Pat. No. 3,709,979. ZSM-22 is described in U.S. Pat. No. 5,336,478. ZSM-23 is described in U.S. Pat. No. 4,076,842. ZSM-35 is described in U.S. Pat. No. 4,016,245. ZSM-48 is described in U.S. Pat. No. 4,375,573, ZSM-50 is described in U.S. Pat. No. 4,640,829, and ZSM-57 is described in U.S. Pat. No. 4,873,067. ZSM-58 is described in U.S. Pat. No. 4,698,217. Constraint index and a method for its determination are described in U.S. Pat. No. 4,016,218, referenced above. The entire contents of each of the aforementioned patents are incorporated herein by reference.

The MCM-22 family material is selected from the group consisting of MCM-22, PSH-3, SSZ-25, MCM-36, MCM-49, MCM-56, ERB-1, EMM-10, EMM-10-P, EMM-12, EMM-13, UZM-8, UZM-8HS, ITQ-1, ITQ-2, ITQ-30, and mixtures of two or more thereof. Materials of the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in EP 0 293 032), ITQ-1 (described in U.S. Pat. No. 6,077,498), and ITQ-2 (described in WO 97/17290), MCM-36 (described in U.S. Pat. No. 5,250,277), MCM-49 (described in U.S. Pat. No. 5,236,575), MCM-56 (described in U.S. Pat. No. 5,362,697), and mixtures of two or more thereof. Related zeolites to be included in the MCM-22 family are UZM-8 (described in U.S. Pat. No. 6,756,030) and UZM-8HS (described in U.S. Pat. No. 7,713,513), both of which are also suitable for use as the molecular sieve of the MCM-22 family.

In one or more embodiments, the microporous crystalline metallosilicate has an Si/M molar ratio (where M is a Group 8, 11, or 13 metal) greater than about 2, or greater than about 25, or greater than about 50, or greater than about 100, or greater than 400, or in the range from about 100 to about 2,000, or from about 100 to about 1,500, or from about 50 to 2,000, or from about 50 to 1,200.

In one or more embodiments, the porous crystalline metallosilicate is crystalline aluminosilicate having a $SiO_2/Al_2O_3$ molar ratio greater than about 3, or greater than about 25, or greater than about 50, or greater than about 100, or greater than about 400, or in the range from about 25 to about 2,000, or from about 50 to about 1,500, or from about 100 to about 1,200, or from about 100 to about 1000, or from about 100 to about 500, or from about 100 to about 400.

In one or more embodiments, the Group 10 metal includes, or is selected from the group consisting of, Ni, Pd, Pt, and mixtures thereof, preferably Pt. The Group 10 metal content of said catalyst composition may be at least 0.005 wt %, based on the weight of the catalyst composition. In one or more embodiments, the Group 10 content is in the range from about 0.005 wt % to about 10 wt %, or from about 0.005 wt % up to about 1.5 wt %, based on the weight of the catalyst composition. The Group 10 metal may be added to the catalyst composition during or after synthesis of the crystalline molecular sieve as any suitable Group 10 metal compound. Thus, for example, where platinum is the, or one of the, Group 10 metals, the platinum may be added as platinum nitrate, chloroplatinic acid, platinous chloride, platinum amine compounds, particularly, tetraamine platinum hydroxide, platinum acetylacetonate, and mixtures of two or more thereof.

In one or more embodiments, the Group 11 metal includes, or is selected from, the group consisting of, silver, gold, copper, and mixtures of two or more thereof, preferably silver. The Group 11 metal content of the catalyst composition is such that the molar ratio of Group 11 metal to Group 10 metal is at least 0.01, based on the molar quantities of each in the catalyst composition. In one or more embodiments, the molar ratio of Group 11 metal to Group 10 metal is in the range from about 0.1 to 10 or from about 0.5 to 5 based on the molar quantities of each in the catalyst composition. The Group 11 metal may be added to the catalyst composition during or after synthesis of the crystalline molecular sieve as any suitable Group 11 metal compound. Thus, for example, where silver is the, or one of the, Group 11 metals, the silver may be added as silver nitrate, silver nitrite, silver acetate, silver hydroxide, silver acetylacetonate, silver carbonate, silver lactate, silver sulfate, silver phosphate, and mixtures of two or more thereof. Where copper is the, or one of the, Group 11 metals, the copper may be added as copper nitrate, copper nitrite, copper acetate, copper hydroxide, copper acetylacetonate, copper carbonate, copper lactate, copper sulfate, copper phosphate, copper chloride, and mixtures of two or more thereof. When Group 10 and/or Group 11 metals are added post synthesis, they may be added by incipient wetness, spray application, solution exchange, chemical vapor disposition, or by other means known in the art.

In one or more embodiments, the molar ratio of said Group 11 metal to Group 10 metal is at least about 0.1, or from at least about 0.1 up to about 10, preferably at least about 0.5, more preferably at least about 1. In one or more embodiments, the Group 11 metal is present as an oxide and the metal is selected from the group consisting of gold, silver, and copper, and mixtures of two or more thereof.

In one or more embodiments, the catalyst composition has an Alpha Value (as measured prior to the addition of the Group 10 metal) of less than 25, preferably less than 15, alternately of greater than about 1 to less than about 25, preferably 1.1 to less than about 15. Alpha Value is determined as described in U.S. Pat. No. 3,354,078; The Journal of Catalysis, v. 4, p. 527, (1965); v. 6, p. 278, (1966); and v. 61, p. 395 (1980) using a constant temperature of 538° C. and a variable flow rate, as described in detail in The Journal of Catalysis, v. 61, p. 395, (1980).

In additional embodiments of the invention, the catalyst composition may further comprise a Group 1 alkali metal (such as Na and/or K) and/or a Group 2 alkaline earth metal (such as Mg, Ca, and/or Ba).

In additional embodiments of the invention, catalyst composition further comprises a Group 1 alkali metal (Na or K) and/or a Group 2 alkaline earth metal (Mg or Ca) and the molar ratio of Group 1 metal to Al in the molecular sieve is at least 0.1.

In one or more embodiments, the molar ratio of Group 1 metal to framework Al in the molecular sieve is at least about 1, or from at least about 1 up to about 3, preferably at least about 2, more preferably at least about 3.

In one or more embodiments, the molar ratio of Group 2 metal to framework Al in the molecular sieve is at least about 1 (preferably 1 to 3, preferably 1 to 2).

In one or more embodiments, the use of any one of the catalyst compositions described herein provides a target conversion of at least about 70%, or at least about 75%, or at least about 80%, or in the range from about 60% to about 80%, of said acyclic $C_5$ feedstock under acyclic $C_5$ conversion conditions, wherein the target conversion is defined as the conversion that would be obtained for an n-pentane feedstock with equimolar $H_2$, a temperature in the range of about 550° C. to about 600° C., an n-pentane partial pressure between 3 and 30 psia at the reactor inlet (21 kPa-a to 207 kPa-a), such as between 3 and 10 psia (21 kPa-a to 69 kPa-a), and an n-pentane weight hourly space velocity between 5 and 20 $hr^{-1}$, such as between 10 and 20 $hr^{-1}$.

In one or more embodiments, the use of any one of the catalyst compositions of this invention provides a carbon selectivity to cyclic $C_5$ compounds of at least about 30%, or at least about 40%, or at least about 50%, or in the range from about 30% to about 50%, under acyclic $C_5$ conversion conditions including an n-pentane feedstock with equimolar $H_2$, a temperature in the range of about 550° C. to about 600° C., an n-pentane partial pressure between 3 and 30 psia at the reactor inlet (21 kPa-a to 207 kPa-a), such as between 10 psia (21 kPa-a to 69 kPa-a), and an n-pentane weight hourly space velocity between 5 and 20 $hr^{-1}$, such as between 10 and 20 $hr^{-1}$.

In one or more embodiments, the use of any one of the catalyst compositions of this invention provides a carbon selectivity to cyclopentadiene of at least about 30%, or at least about 40%, or at least about 50%, or in the range from about 30% to about 50%, under acyclic $C_5$ conversion conditions including an n-pentane feedstock with equimolar $H_2$, a temperature in the range of about 550° C. to about 600° C., an n-pentane partial pressure between 3 and 30 psia at the reactor inlet (21 kPa-a to 207 kPa-a), such as between 3 and 10 psia (21 kPa-a to 69 kPa-a) and an n-pentane weight hourly space velocity between 5 and 20 $hr^{-1}$, such as between 10 and 20 $hr^{-1}$.

Useful catalyst compositions comprise a crystalline aluminosilicate, which is optionally combined with one, two, or more additional metals or metal compounds. Preferred combinations include: platinum on MFI silversilicate, platinum on coppersilicate MFI, platinum with silver on ZSM-5, and platinum with copper on ZSM-5.

The catalyst compositions of this invention can be combined with a matrix or binder material to render them attrition resistant and more resistant to the severity of the conditions to which they will be exposed during use in hydrocarbon conversion applications. The combined compositions can contain 1 to 99 wt % of the materials of the invention based on the combined weight of the matrix (binder) and material of the invention. The relative proportions of finely divided crystalline material and inorganic oxide gel matrix vary widely, with the crystal content ranging from about 1 to about 90 wt % and more usually, particularly when the composite is prepared in the form of beads, in the range of about 2 to about 80 wt % of the composite.

During the use of the catalyst compositions in the processes of this invention, coke may be deposited on the catalyst compositions, whereby such catalyst compositions lose a portion of its catalytic activity and become deactivated. The deactivated catalyst compositions may be regenerated by conventional techniques including high pressure hydrogen treatment and combustion of coke on the catalyst compositions with an oxygen-containing gas.

Catalyst composition shape and design are preferably configured to minimize pressure drop, increase heat transfer, and minimize mass transport phenomena during use. Suitable catalyst shape and design are described in WO 2014/053553, which is incorporated herein by reference. The catalyst composition may, optionally, be an extrudate with a diameter of 2 mm to 20 mm. Optionally, the catalyst composition cross section may be shaped with one or more lobes and/or concave sections. Additionally, the catalyst composition lobes and/or concave sections may be spiraled. The catalyst composition may be an extrudate with a diameter of 2 mm to 20 mm; and the catalyst composition cross section may be shaped with one or more lobes and/or concave sections; and the catalyst composition lobes and/or concave sections may be spiraled. For fixed bed reactors (fired tube, convective tube, and cyclic) lobed, concave, spiral, etc., particle shapes are particularly useful and for fluid bed reactors spherical particle shapes are particularly useful. Preferably, particles for a fixed bed (e.g., cyclic fixed bed reactor, fired tubes reactor, convectively heated tubes reactor, etc.) are typically an extrudate with a diameter of 2 mm to 20 mm; and the catalyst composition cross section may be shaped with one or more lobes and/or concave sections; and the catalyst composition lobes and/or concave sections may be spiraled.

In various aspects, the catalyst material (and optional matrix material) may have an average diameter of about 5 μm to about 50 mm, such as about 25 μm to about 3500 μm. Preferably, the catalyst material (and optional matrix or binder) may have an average diameter of about 25 μm to about 1200 μm, more preferably about 50 μm to about 1000 μm, more preferably about 10 μm to about 500 μm, more preferably about 30 μm to about 400 μm, more preferably about 40 μm to about 300 μm.

"Average diameter" for particles in the range of 1 to 3500 μm is determined using a Mastersizer™ 3000 available from Malvern Instruments, Ltd., Worcestershire, England. Unless otherwise stated, particle size is determined at D50. D50 is the value of the particle diameter at 50% in the cumulative distribution. For example, if D50=5.8 um, then 50% of the particles in the sample are equal to or larger than 5.8 um and 50% are smaller than 5.8 um. (In contrast, if D90=5.8 um, then 10% of the particles in the sample are larger than 5.8 um and 90% are smaller than 5.8 um.) "Average diameter" for particles in the range of more than 3.5 mm to 50 mm is determined using a micrometer on a representative sample of 100 particles.

INDUSTRIAL APPLICABILITY

The first hydrocarbon reactor effluent obtained during the acyclic $C_5$ conversion process containing cyclic, branched, and linear $C_5$ hydrocarbons and, optionally, containing any combination of hydrogen, $C_4$ and lighter byproducts, or $C_6$ and heavier byproducts is a valuable product in and of itself. Preferably, CPD and/or DCPD may be separated from the reactor effluent to obtain purified product streams which are useful in the production of a variety of high value products.

For example, a purified product stream containing 50 wt % or greater, or preferably 60 wt % or greater of DCPD is useful for producing hydrocarbon resins, unsaturated polyester resins, and epoxy materials. A purified product stream containing 80 wt % or greater, or preferably 90 wt % or greater of CPD is useful for producing Diels-Alder reaction products formed in accordance with the following reaction Scheme (I):

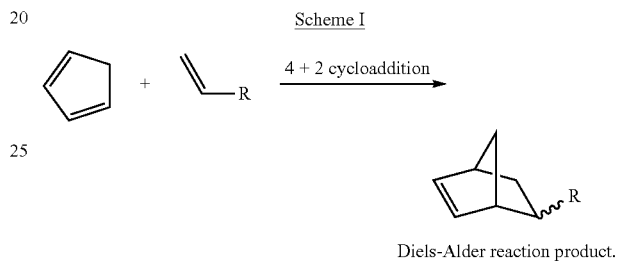

where R is a heteroatom or substituted heteroatom, substituted or unsubstituted $C_1$-$C_{50}$ hydrocarbyl radical (often a hydrocarbyl radical containing double bonds), an aromatic radical, or any combination thereof. Preferably, substituted radicals or groups contain one or more elements from Groups 13-17, preferably from Groups 15 or 16, more preferably nitrogen, oxygen, or sulfur. In addition to the monoolefin Diels-Alder reaction product depicted in Scheme (I), a purified product stream containing 80 wt % or greater, or preferably 90 wt % or greater of CPD can be used to form Diels-Alder reaction products of CPD with one or more of the following: another CPD molecule, conjugated dienes, acetylenes, allenes, disubstituted olefins, trisubstituted olefins, cyclic olefins and substituted versions of the foregoing. Preferred Diels-Alder reaction products include norbornene, ethylidene norbornene, substituted norbornenes (including oxygen containing norbornenes), norbornadienes, and tetracyclododecene, as illustrated in the following structures:

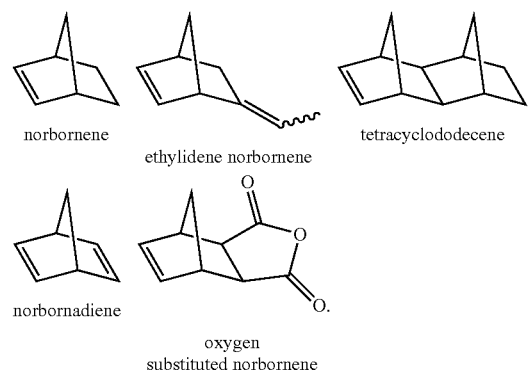

The foregoing Diels-Alder reaction products are useful for producing polymers and copolymers of cyclic olefins copolymerized with olefins such as ethylene. The resulting cyclic olefin copolymer and cyclic olefin polymer products are useful in a variety of applications, e.g., packaging film.

A purified product stream containing 99 wt % or greater of DCPD is useful for producing DCPD polymers using, for example, ring opening metathesis polymerization (ROMP) catalysts. The DCPD polymer products are useful in forming articles, particularly molded parts, e.g., wind turbine blades and automobile parts.

Additional components may also be separated from the reactor effluent and used in the formation of high value products. For example, separated cyclopentene is useful for producing polycyclopentene, also known as polypentenamer, as depicted in Scheme (II).

Scheme II

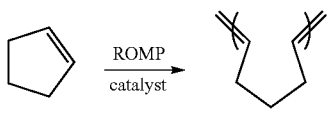

Separated cyclopentane is useful as a blowing agent and as a solvent. Linear and branched $C_5$ products are useful for conversion to higher olefins and alcohols. Cyclic and non cyclic $C_5$ products, optionally after hydrogenation, are useful as octane enhancers and transportation fuel blend components.

EXAMPLES

The following examples illustrate the present invention. Numerous modifications and variations are possible and it is to be understood that within the scope of the appended claims, the invention may be practiced otherwise than as specifically described herein.

Measurement of Total Surface Area by BET

The total BET was measured by nitrogen adsorption/desorption with a Micromeritics Tristar II 3020 instrument after degassing of the calcined zeolite powders for 4 hrs at 350° C. More information regarding the method can be found, for example, in "Characterization of Porous Solids and Powders: Surface Area, Pore Size and Density", S. Lowell et al., Springer, 2004.

X-Ray Diffraction Patterns

The X-ray diffraction data (powder XRD or XRD) were collected with a Bruker D4 Endeavor diffraction system with a VÅNTEC multichannel detector using copper K-alpha radiation. The diffraction data were recorded by scanning mode with 0.018 degrees two-theta, where theta is the Bragg angle, and using an effective counting time of about 30 seconds for each step.

Comparative Example 1: Synthesis of ZSM-5/0.45 wt % Pt

A synthesis mixture with ~20.3% solids was prepared from 10,000 g of deionized (DI) water, 600 g of 50% NaOH solution, 25 g of 45% sodium aluminate solution, 730 g of n-propyl amine 100% solution, 80 g of ZSM-5 seed crystals, and 3,190 g of Ultrasil PM™ Modified silica (which contains trace amounts of alumina) were mixed in a 5-gal pail container and then charged into a 5-gal autoclave after mixing. The synthesis mixture had the following molar composition:

| | |
|---|---|
| $SiO_2/Al_2O_3$ | ~470 |
| $H_2O/SiO_2$ | ~12.1 |
| $OH/SiO_2$ | ~0.16 |
| $Na/SiO_2$ | ~0.16 |
| n-PA/Si | ~0.25. |

Figure 1B:
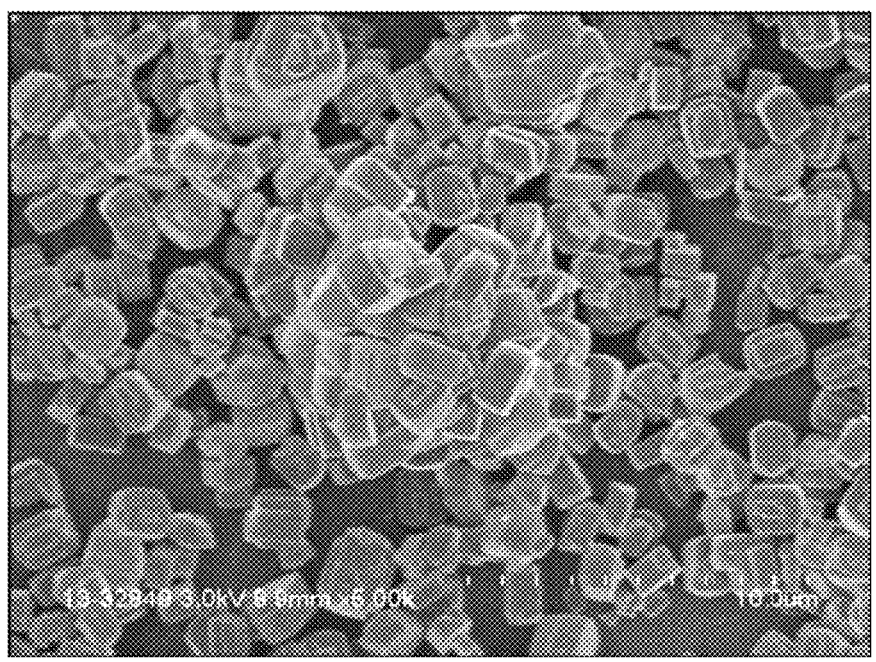
FIG. 1B shows a scanning electron microscope (SEM) image of the as-synthesized ZSM-5 produced in Comparative Example 1.

The synthesis mixture was reacted at 230° F. (110° C.) at 250 rpm for 72 hours. The resulting product was filtered and washed with DI water and then dried in the oven at ~250° F. (121° C.) overnight. The XRD pattern of the as-synthesized material showed the typical pure phase of ZSM-5 topology (shown in FIG. 1A). The SEM shown in FIG. 1B is of the as-synthesized material and shows that the material was composed of mixture of large crystals with size of ~2 micron. A portion of the as-synthesized crystals were converted (for characterization) into the hydrogen form by three ion exchanges with ammonium nitrate solution at room temperature, followed by drying at 250° F. (121° C.) and calcination at 1000° F. (540° C.) for 6 hours. The resulting ZSM-5 crystals had a $SiO_2/Al_2O_3$ molar ratio of ~414, total surface area (SA)/(micropore SA+mesopore SA) of 490 (440+51) $m^2/g$, hexane sorption of 117 mg/g and an Alpha value (as measured on the proton form) of 31. A second portion of the material was used as synthesized for Pt impregnation.

ZSM-5 having a $SiO_2/Al_2O_3$ molar ratio of 414 and a sodium content of 0.38 wt % was calcined for 6 hours in nitrogen at 900° F. (482° C.). After cooling, the sample was re-heated to 900° F. (482° C.) in nitrogen and held for three hours. The atmosphere was then gradually changed to 1.1, 2.1, 4.2, and 8.4% oxygen in four stepwise increments. Each step was held for 30 minutes. The temperature was increased to 1000° F. (540° C.), the oxygen content was increased to 16.8%, and the material was held at 1000° F. (540° C.) for 6 hours. After cooling, 0.5 wt % Pt was added via incipient wetness impregnation using an aqueous solution of tetraamine platinum hydroxide. The catalyst composition was dried in air at room temperature for 2 hours, then at 250° F. (121° C.) for 4 hours, and lastly calcined in air at 660° F. (349° C.) for 3 hours. The catalyst composition powder was pressed (15 ton), crushed, and sieved to obtain 20-40 mesh particle size.

Example 2: Synthesis of ZSM-5/0.45 wt % Pt/0.28 wt % Ag

A mixture with about 22% solids was prepared from 8800 g of deionized (DI) water, 600 g of 50% NaOH solution, 26 g of 45% sodium aluminate solution, 730 g of n-propyl amine 100% solution, 40 g of ZSM-5 seed crystals, and 3,190 g of Ultrasil PM Modified silica in a 5-gal pail container and then charged into a 5-gal autoclave after mixing. The mixture had the following molar composition:

| | |
|---|---|
| $SiO_2/Al_2O_3$ | ~470 |
| $H_2O/SiO_2$ | ~12.1 |
| $OH/SiO_2$ | ~0.16 |
| $Na/SiO_2$ | ~0.16 |
| n-PA/Si | ~0.25. |

Figure 2A:
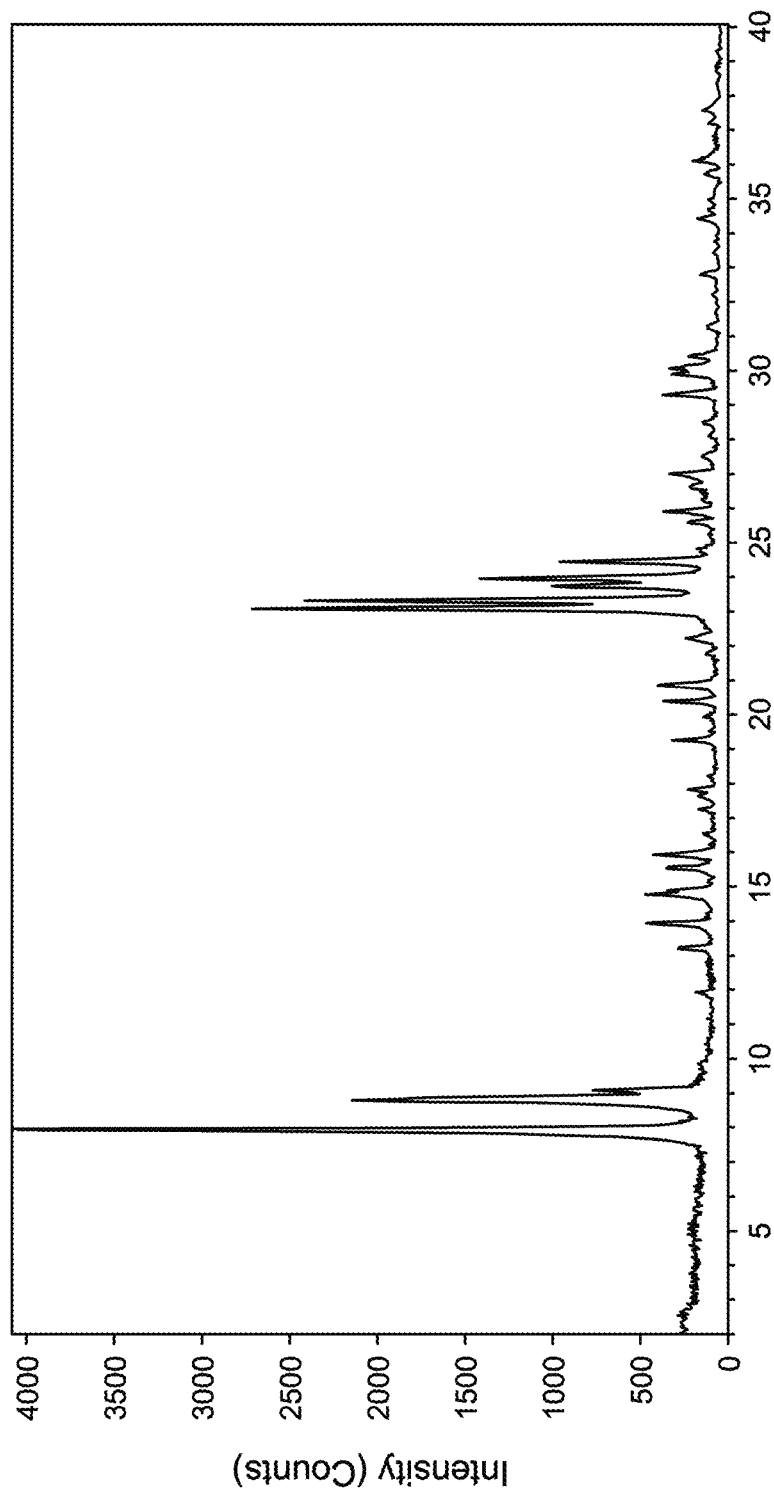
FIG. 2A shows an X-ray diffraction (XRD) pattern of the as-synthesized ZSM-5 produced in Example 2.
Figure 2B:
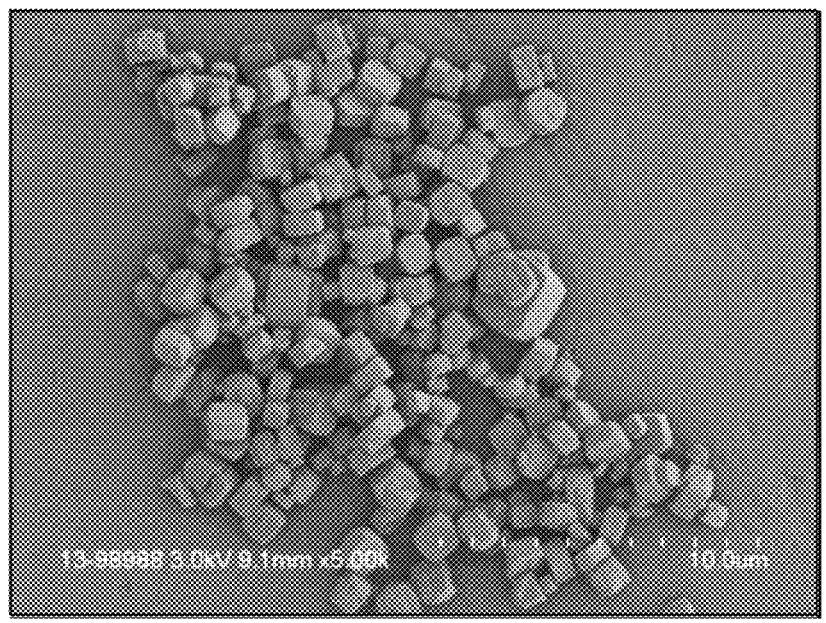
FIG. 2B shows a scanning electron microscope (SEM) image of the as-synthesized ZSM-5 produced in Example 2.

The mixture was reacted at 230° F. (110° C.) at 250 rpm for 72 hours. The resulting products were filtered and washed with deionized water, then dried overnight at 250° F. (121° C.). The XRD pattern of the as-synthesized material showed the typical pure phase of ZSM-5 topology, see FIG. 2A. The SEM of the as-synthesized material, see FIG. 2B, shows that the material was composed of a mixture of large crystals with a size of 1 to 2 microns. The resulting ZSM-5 crystals had a $SiO_2/Al_2O_3$ molar ratio of ~400, total surface area(SA)/(micropore SA+mesopore SA) of 468 (422+45) $m^2/g$.

The resultant material was calcined for 6 hours in nitrogen at 900° F. (482° C.). After cooling, the sample was re-heated to 900° F. (482° C.) in nitrogen and held for three hours. The atmosphere was then gradually changed to 1.1, 2.1, 4.2, and 8.4% oxygen in four stepwise increments. Each step was followed by a thirty minute hold. The temperature was increased to 1000° F. (540° C.), the oxygen content was increased to 16.8%, and the material was held at 1000° F. (540° C.) for 6 hours. After cooling, 0.282 wt % Ag was added via incipient wetness impregnation using an aqueous solution of silver nitrate. The sample was dried for four hours at 250° F. (121° C.). Subsequently, 0.45 wt % Pt was added via incipient wetness impregnation using an aqueous solution of tetraamine platinum hydroxide. The catalyst was dried in air at room temperature then at 250° F. (121° C.), and calcined in air for one hour at 610° F. (321° C.). The catalyst powder was pressed (15 ton), crushed, and sieved to obtain 40-60 mesh particle size.

Example 3: Synthesis of [0.96 wt % Ag]-MFI/0.5 wt % Pt

A mixture with about 22% solids was prepared from 950 g of DI water, 53.5 g of 50% NaOH solution, 76.8 g of n-propyl amine 100% solution, 10 g of ZSM-5 seed crystals, and 336 g of Ultrasil PM Modified silica, and 4.4 g of silver nitrate in a 2-liter container and then charged into a 2-liter autoclave after mixing. The mixture had the following molar composition:

| | |
|---|---|
| $SiO_2/Al_2O_3$ | >1000 |
| $H_2O/SiO_2$ | ~10.98 |
| $OH/SiO_2$ | ~0.17 |
| $Na/SiO_2$ | ~0.17 |
| n-PA/Si | ~0.25. |

Figure 3A:
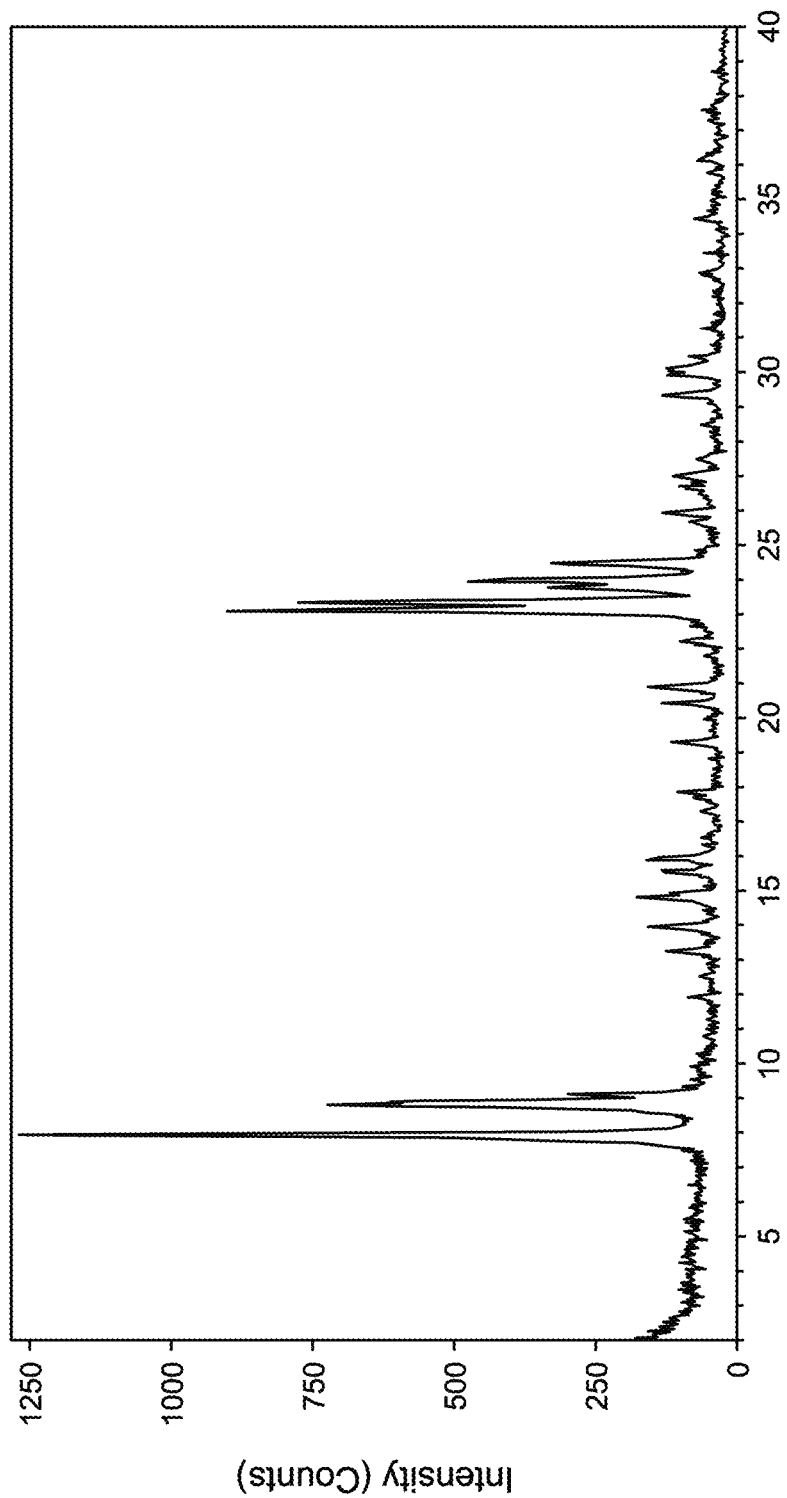
FIG. 3A shows an X-ray diffraction (XRD) pattern of the as-synthesized silversilicate MFI material produced in Example 3.
Figure 3B:
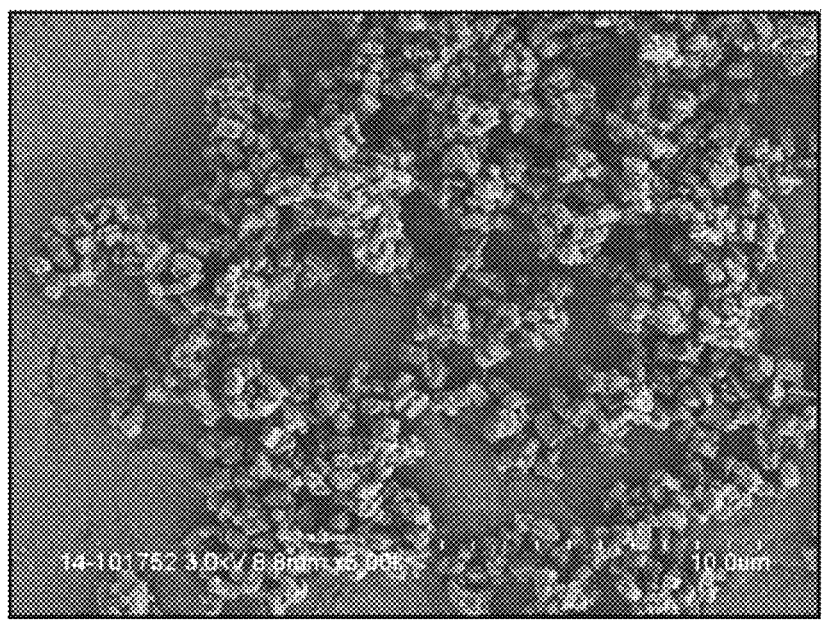
FIG. 3B shows a scanning electron microscope (SEM) image of the as-synthesized silversilicate MFI material produced in Example 3.

The mixture was reacted at 230° F. (110° C.) at 250 rpm for 72 hours. The resulting products were filtered and washed with deionized water then dried overnight at 250° F. (121° C.). The XRD pattern of the as-synthesized material showed the typical pure phase of an MFI type microporous crystalline material, see FIG. 3A. The SEM of the as-synthesized material, see FIG. 3B, shows that the material was composed of a mixture of large crystals with a size of less than 1 micron. The resulting crystals had a $SiO_2/Al_2O_3$ molar ratio of >800, Na of ~0.28%, and Ag of 0.9 wt %.

The resultant material was calcined for 6 hours in nitrogen at 900° F. (482° C.). After cooling, the sample was re-heated to 900° F. (482° C.) in nitrogen and held for three hours. The atmosphere was then gradually changed to 1.1, 2.1, 4.2, and 8.4% oxygen in four stepwise increments. Each step was followed by a thirty minute hold. The temperature was increased to 1000° F. (540° C.), the oxygen content was increased to 16.8%, and the material was held at 1000° F. (540° C.) for 6 hours. After cooling, 0.45 wt % Pt was added via incipient wetness impregnation using an aqueous solution of tetraamine platinum hydroxide. The catalyst was dried in air at room temperature then at 250° F. (121° C.), and calcined in air for three hours at 660° F. (349° C.). The catalyst powder was pressed (15 ton), crushed, and sieved to obtain 40-60 mesh particle size.

Example 4: Catalytic Testing of Comparative Example 1 Material

To test the performance of the Comparative Example 1 material (ZSM-5/0.45% Pt), the catalyst (0.5 g) was physically mixed with quartz (1.5 g, 60-80 mesh) and loaded into a 3/8" OD, 18" long stainless steel reactor. The catalyst bed was held in place with quartz wool and the reactor void space was loaded with coarse quartz particles. The reactor was loaded onto the unit and pressure tested to ensure no leaks. The catalyst was dried for 1 hour under He (100 mL/min, 30 psig, 250° C.) then reduced for 1 hour under $H_2$ (200 mL/min, 30 psig, 500° C.). The catalyst was then tested for performance with feed of n-pentane, $H_2$, and balance He, typically at 550-600° C., 5.0 psia (35 kPa-a) $C_5H_{12}$, 1.0 molar $H_2:C_5H_{12}$, 14.7 $h^{-1}$ WHSV, and 30 psig (207 kPa) total. Catalyst stability and regenerability were tested post initial tests at 550-600° C. by treatment with $H_2$ (200 mL/min, 30 psig (207 kPa), 650° C.) for 5 h then re-testing performance at 600° C. Experiments were conducted at high WHSV (~15 $h^{-1}$) to enable observation of catalytic activity and deactivation differences between catalyst candidates. Operation at lower WHSV would be expected to give higher yields of CPD.

The results of the catalytic testing are summarized in Table 1 and show that at 595° C. the catalyst produced greater than 80% conversion of pentane, with 50% selectivity to cyclic $C_5$ species and 39% selectivity to CPD. Yield to cracking products is between 13 and 17 C %.

TABLE 1

| Temperature (° C.) | Conversion (%) $C_5H_{12}$ | Selectivity (C %) | | | | Yield (C %) | | | |
|---|---|---|---|---|---|---|---|---|---|
| | | $cC_5$ | CPD | $C_1$ | $C_{2-4}$ | $cC_5$ | CPD | $C_1$ | $C_{2-4}$ |
| 545 | 71 | 40 | 24 | 2.8 | 15 | 28 | 17 | 2.0 | 11 |
| 570 | 80 | 45 | 32 | 3.1 | 16 | 36 | 26 | 2.5 | 13 |
| 595 | 84 | 50 | 39 | 3.3 | 16 | 42 | 33 | 2.8 | 14 |
| 595, Post $H_2$ | 76 | 48 | 38 | 4.1 | 17 | 37 | 29 | 3.1 | 13 |

Example 5: Catalytic Testing of Example 2 Material

Figure 4:
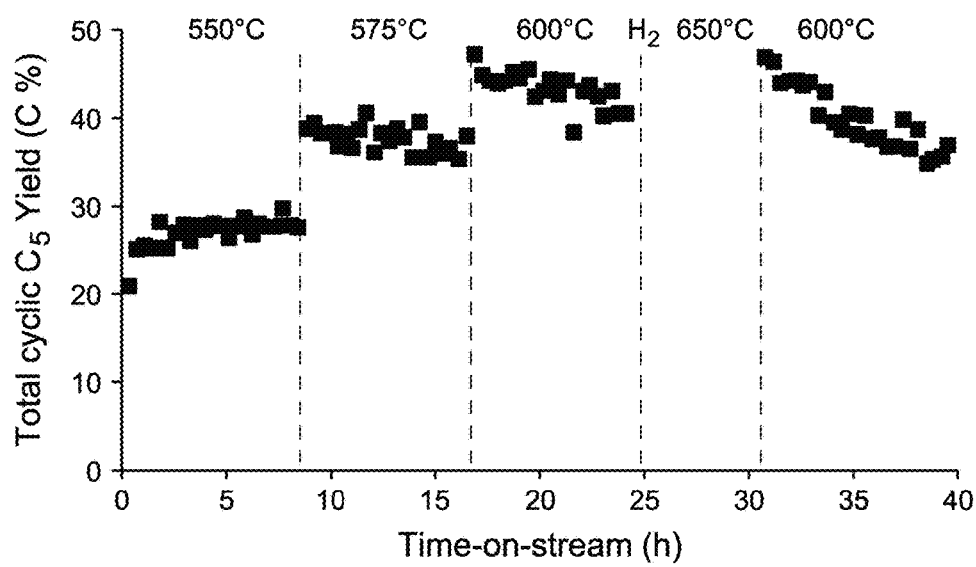
FIG. 4 is a graph showing the yield of cyclic $C_5$ hydrocarbons at varying temperatures before and after hydrogen treatment obtained in the catalytic testing of Example 5.

The catalytic testing described in Example 4 was repeated with the Example 2 material (ZSM-5/0.45 wt % Pt/0.28 wt % Ag) and the results are summarized in Table 2 and FIG. 4. Table 2 shows that at 600° C. the catalyst of Example 2 produced greater than 80% conversion of pentane, with 51% selectivity to cyclic $C_5$ species and 42% selectivity to CPD. FIG. 4 shows this activity is stable over 8 hours at each temperature with a faster rate of deactivation after 5 hours of $H_2$ treatment at 650° C. This performance is greatly superior to other dehydrogenation catalysts, aluminas and aluminates, as discussed above, as well as superior to the catalyst of Comparative Example 1. The catalyst also produces $C_1$ and $C_{2-4}$ cracking products. These are lower value, undesired side products that cannot be recycled in this process, but can be separated and used as feedstock for other processes or as fuels. However, yield to cracking products is less than 12% (significantly better than the catalyst of Comparative Example 1) while the ratio of $C_5$ cyclic products to cracking products is nearly 4.0 or greater at each condition tested and notably higher after 5 hours of $H_2$ treatment at 650° C.

TABLE 2

| Temperature (° C.) | Conversion (%) $C_5H_{12}$ | Selctivity (C %) | | | | Yield (C %) | | | | $cC_5:C_{1-4}$ |
|---|---|---|---|---|---|---|---|---|---|---|
| | | $cC_5$ | CPD | $C_1$ | $C_{2-4}$ | $cC_5$ | CPD | $C_1$ | $C_{2-4}$ | |
| 550 | 66 | 41 | 25 | 0.8 | 6.8 | 27 | 16 | 0.6 | 4.5 | 5.3 |
| 575 | 79 | 48 | 34 | 1.5 | 11 | 38 | 27 | 1.2 | 8.7 | 3.8 |
| 600 | 84 | 51 | 42 | 1.8 | 12 | 43 | 35 | 1.5 | 10 | 3.7 |
| 600, Post $H_2$ | 71 | 56 | 46 | 1.3 | 7.0 | 40 | 33 | 0.9 | 4.9 | 6.8 |

Example 6: Catalytic Testing of Example 3 Material

Figure 5:
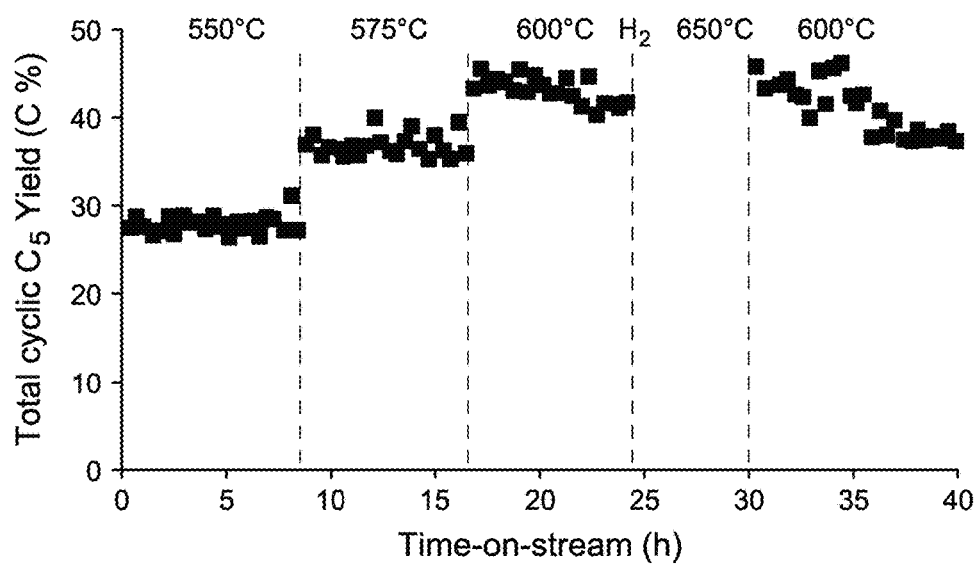
FIG. 5 is a graph showing the yield of cyclic $C_5$ hydrocarbons at varying temperatures before and after hydrogen treatment obtained in the catalytic testing of Example 6.

The catalytic testing described in Example 4 was repeated with the Example 3 material ([0.96 wt % Ag]-MFI/0.5 wt % Pt) and the results are summarized in Table 3 and FIG. 5. Table 3 shows that at 600° C. the catalyst of Example 3 produced greater than 80% conversion of pentane, with 52% selectivity to cyclic $C_5$ species and 38% selectivity to CPD. FIG. 5 shows this activity is stable over 8 hours at each temperature and after 5 hours of $H_2$ treatment at 650° C. Activity decreases post-$H_2$ treatment at longer time-on-stream. Yield to cracking products is less than 12% while the ratio of $C_5$ cyclic products to cracking products is greater than 3.0 at each condition tested. Again, this performance is greatly superior to other conventional dehydrogenation catalysts, aluminas and aluminates, as discussed above as well as the catalyst of Comparative Example 1.

TABLE 3

| Temperature (° C.) | Conversion (%) $C_5H_{12}$ | Selectivity (C %) | | | | Yield (C %) | | | | $cC_5:C_{1-4}$ |
|---|---|---|---|---|---|---|---|---|---|---|
| | | $cC_5$ | CPD | $C_1$ | $C_{2-4}$ | $cC_5$ | CPD | $C_1$ | $C_{2-4}$ | |
| 550 | 63 | 44 | 22 | 0.9 | 7.9 | 28 | 14 | 0.6 | 5.0 | 5.0 |
| 575 | 75 | 49 | 30 | 1.4 | 11 | 37 | 23 | 1.1 | 8.0 | 4.1 |
| 600 | 82 | 52 | 38 | 1.8 | 12 | 43 | 31 | 1.5 | 10 | 3.7 |
| 600, Post $H_2$ | 77 | 52 | 39 | 2.7 | 13 | 41 | 30 | 2.1 | 10 | 3.3 |

Example 7: Long Term Stability Testing of Example 3 Material

Figure 6:
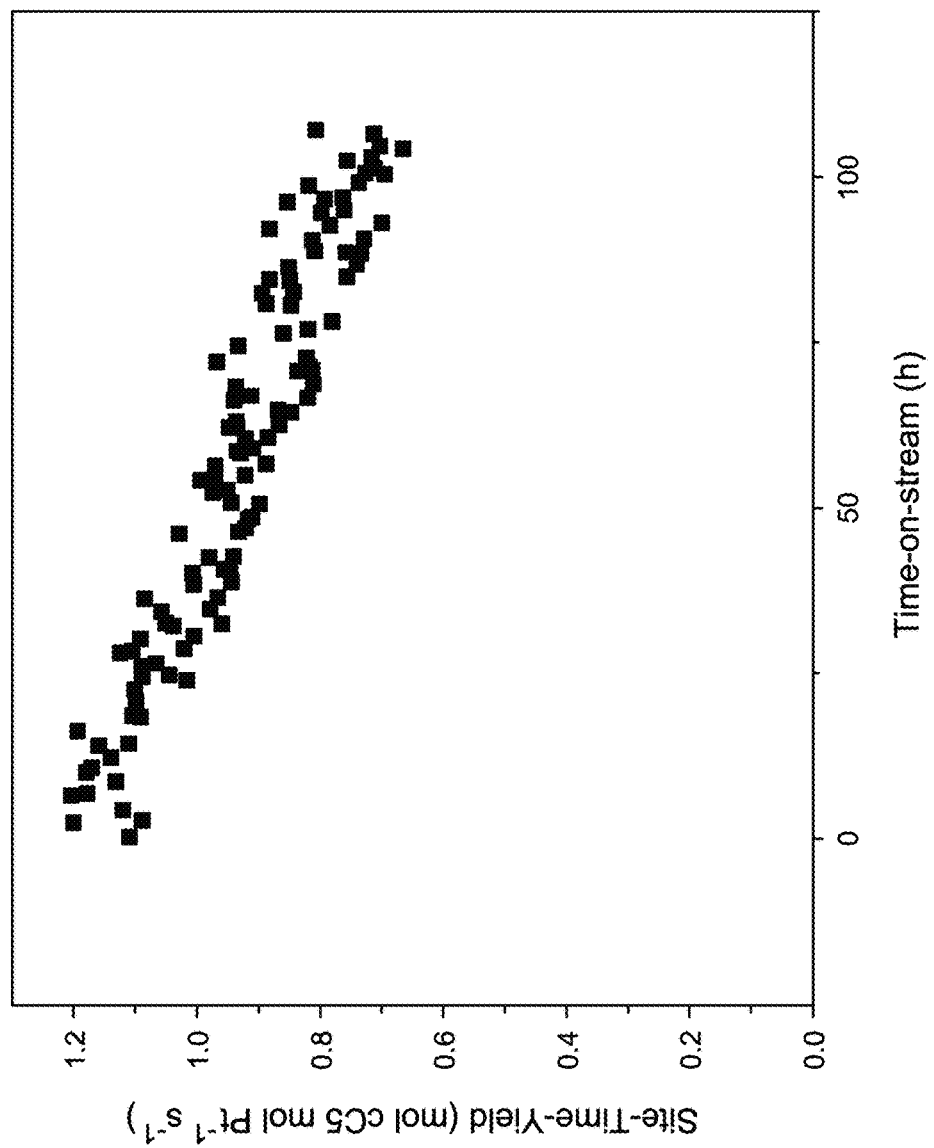
FIG. 6 is a graph of site-time-yield of cyclic $C_5$ hydrocarbons with time on stream at 600° C. with alternating on-oil and $H_2$ treatment cycles of one hour each for the catalytic testing of Example 7.

The long term stability of the Example 3 material ([0.96% Ag]-MFI/0.5% Pt) was tested at 600° C. over 100 hours with in-situ $H_2$ treatment and on-oil periods switching every hour. 0.5 gm of the catalyst of Example 3 was tested at 5.0 psia (35 kPa-a) $C_5H_{12}$, 1:1 molar $H_2$:$C_5$, 14.7 WHSV, and 45 psia total (310 kPa-a) during on-oil period; 200 cm³ min⁻¹ $H_2$ at 600° C. and 45 psia total (310 kPa-a) (no balance) during $H_2$ treatment cycle. FIG. 6 shows the catalyst retained about 60% of its fresh activity in terms of cyclic $C_5$ site-time-yields (mol cyclic $C_5$/mol Pt/sec) after 107 hours total time-on-stream.

Example 8: Synthesis of ZSM-5/0.43 wt % Pt/0.16 wt % Cu

The synthesis of Example 2 was repeated except the silver impregnation was replaced by adding 0.16 wt % Cu via incipient wetness impregnation using an aqueous solution of copper (II) nitrate hydrate. The sample was dried for four hours at 250° F. (121° C.). Subsequently, 0.43 wt % Pt was added via incipient wetness impregnation using an aqueous solution of tetraamine platinum hydroxide. The catalyst was dried in air at room temperature then at 250° F. (121° C.), and calcined in air for one hour at 610° F. (321° C.).

Example 9: Synthesis of [0.74 wt % Cu]-MFI/0.5 wt % Pt

A mixture with ~22% solids was prepared from 940 g of DI water, 53.5 g of 50% NaOH solution, 76.8 g of n-propyl amine 100% solution, 10 g of ZSM-5 seed crystals, and 336 g of Ultrasil PM Modified silica, and 8.8 g of copper nitrate hydrate were mixed in a 2-liter container and then charged into a 2-liter autoclave after mixing. The mixture had the following molar composition:

| | |
|---|---|
| $SiO_2/Al_2O_3$ | >1000 |
| $H_2O/SiO_2$ | ~10.98 |
| $OH/SiO_2$ | ~0.17 |
| $Na/SiO_2$ | ~0.17 |
| n-PA/Si | ~0.25. |

Figure 7A:
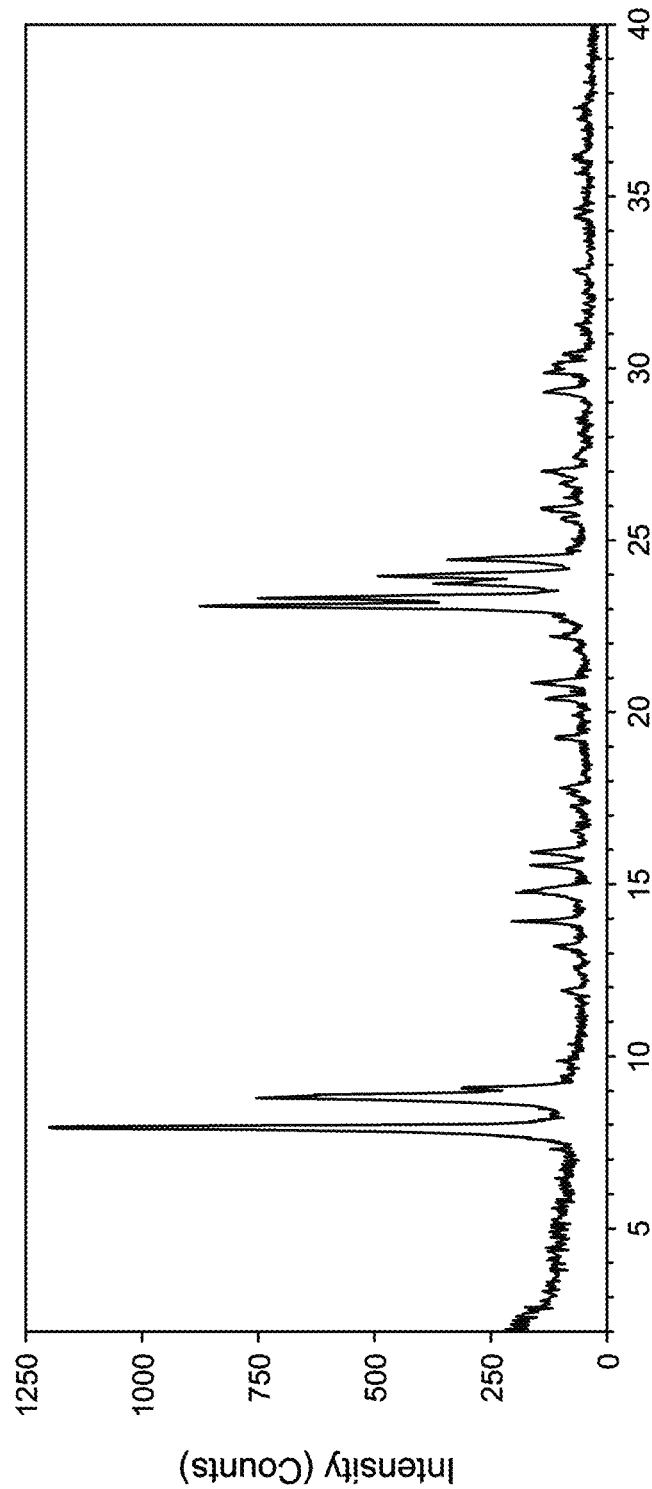
FIG. 7A shows an X-ray diffraction (XRD) pattern of the as-synthesized coppersilicate MFI material produced in Example 9.
Figure 7B:
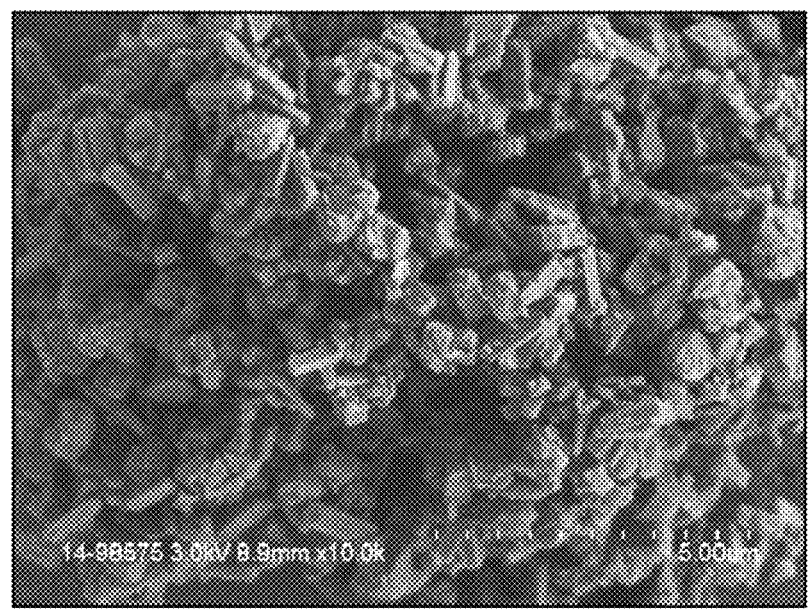
FIG. 7B shows a scanning electron microscope (SEM) image of the as-synthesized coppersilicate MFI material produced in Example 9.

The mixture was reacted at 230° F. (110° C.) at 250 rpm for 72 hours. The resulting products were filtered & washed with DI water and then dried in the oven at ~250° F. (121° C.) overnight. The XRD pattern of the as-synthesized material showed the typical pure phase of an MFI type microporous crystalline material, see FIG. 7A. The SEM of the as-synthesized material, see FIG. 7B shows that the material was composed of a mixture of large crystals with a size of less than 1 micron. The resulting crystals had a $SiO_2/Al_2O_3$ molar ratio of >800, Na of ~00.48%, and Cu of 0.75 wt %.

This material was calcined for 6 hours in nitrogen at 900° F. (482° C.). After cooling, the sample was re-heated to 900° F. (482° C.) in nitrogen and held for three hours. The atmosphere was then gradually changed to 1.1, 2.1, 4.2, and 8.4% oxygen in four stepwise increments. Each step was followed by a thirty minute hold. The temperature was increased to 1000° F., the oxygen content was increased to 16.8%, and the material was held at 1000° F. (540° C.) for 6 hours. Subsequently, 0.51 wt % Pt was added via incipient wetness impregnation using an aqueous solution of tetraamine platinum hydroxide. The catalyst was dried in air at room temperature then at 250° F. (121° C.), and calcined in air for three hours at 660° F. (349° C.).

Example 10: Catalytic Testing of Example 9 Material

Figure 8:
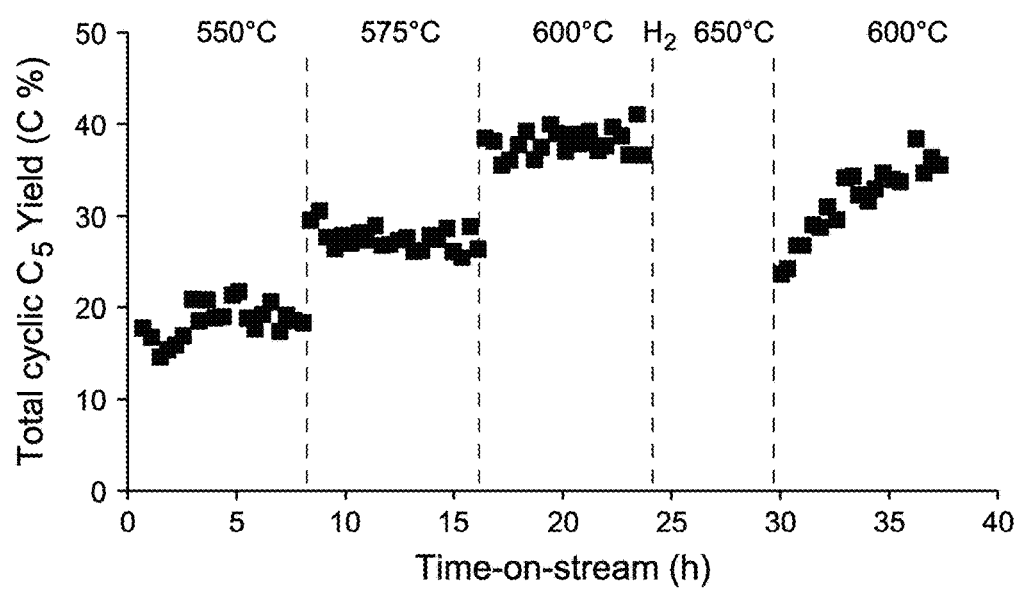
FIG. 8 is a graph showing the yield of cyclic $C_5$ hydrocarbons at varying temperatures before and after hydrogen treatment obtained in the catalytic testing of Example 10.

The catalytic testing described in Example 4 was repeated with the Example 9 material ([0.74 wt % Cu]-MFI/0.5 wt % Pt) and the results are summarized in Table 4 and FIG. 8. Table 4 shows that at 600° C. the catalyst of Example 9 produced nearly 80% conversion of pentane, with 48% selectivity to cyclic $C_5$ species and 38% selectivity to CPD. FIG. 8 shows this activity is stable over 8 hours at each temperature and after 5 hours of $H_2$ treatment at 650° C. Activity is initially lower post-$H_2$ treatment but increases to pre-$H_2$ treatment values at longer time-on-stream. [0.74% Cu]-MFI/0.5% Pt also produces $C_1$ and $C_{2-4}$ cracking products. However, yield to cracking products is less than 6% while the ratio of $C_5$ cyclic products to cracking products is nearly greater than 7 at each condition tested. This performance is greatly superior to other conventional dehydrogenation catalysts, aluminas and aluminates, as discussed above and also superior to the catalyst of Comparative Example 1

TABLE 4

| Temperature (° C.) | Conversion (%) $C_5H_{12}$ | Selectivity (C %) | | | | Yield (C %) | | | | $cC_5:C_{1-4}$ |
|---|---|---|---|---|---|---|---|---|---|---|
| | | $cC_5$ | CPD | $C_1$ | $C_{2-4}$ | $cC_5$ | CPD | $C_1$ | $C_{2-4}$ | |
| 550 | 58 | 32 | 19 | 0.4 | 4.0 | 18 | 11 | 0.2 | 2.4 | 7.2 |
| 575 | 69 | 40 | 28 | 0.5 | 4.9 | 27 | 19 | 0.3 | 3.4 | 7.3 |
| 600 | 79 | 48 | 38 | 0.6 | 6.5 | 38 | 30 | 0.5 | 5.1 | 6.8 |
| 600, Post $H_2$ | 62 | 51 | 41 | 0.5 | 4.3 | 32 | 26 | 0.3 | 2.7 | 10.5 |

All documents described herein are incorporated by reference herein, including any priority documents and/or testing procedures to the extent they are not inconsistent with this text. As is apparent from the foregoing general description and the specific embodiments, while forms of the invention have been illustrated and described, various modifications can be made without departing from the spirit and scope of the invention. Accordingly, it is not intended that the invention be limited thereby. Likewise, the term "comprising" is considered synonymous with the term "including." Likewise whenever a composition, an element or a group of elements is preceded with the transitional phrase "comprising," it is understood that we also contemplate the same composition or group of elements with transitional phrases "consisting essentially of," "consisting of," "selected from the group consisting of," or "is" preceding the recitation of the composition, element, or elements and vice versa.

What is claimed is:

1. A process for producing cyclic $C_5$ compounds including cyclopentadiene, the process comprising:
   (a) contacting a feed containing acyclic $C_5$ hydrocarbons with a catalyst comprising (i) a microporous crystalline metallosilicate having a constraint index less than or equal to 12, (ii) a Group 10 metal or a compound thereof, and (iii) a Group 11 metal or a compound thereof under conditions effective to convert at least part of the acyclic $C_5$ hydrocarbons in the feed to produce an effluent comprising cyclopentadiene, wherein the microporous crystalline metallosilicate comprises a metallosilicate framework type selected from the group consisting of MWW, MFI, LTL, MOR, BEA, TON, MTW, MTT, FER, MRE, MFS, MEL, DDR, EUO, and FAU; and
   (b) recovering cyclopentadiene from the effluent.

2. The process of claim 1, wherein the microporous crystalline metallosilicate has a constraint index from 1 to 12.

3. The process of claim 1, wherein the Group 10 metal is selected from the group consisting of Ni, Pd, Pt, and mixtures thereof.

4. The process of claim 1, wherein the Group 10 metal is present in an amount in the range from about 0.005 wt % to about 10 wt % based on the weight of the catalyst composition.

5. The process of claim 1, wherein the catalyst also contains a Group 1 alkali metal and/or a Group 2 alkaline earth metal.

6. The process of claim 1, wherein the Group 11 metal is selected from the group consisting of silver, gold, copper, and mixtures thereof.

7. The process of claim 1, wherein the Group 11 metal is present at a molar ratio of Group 11 metal to Group 10 metal of about 0.1 to about 5.

8. The process of claim 1, wherein the effluent also includes cyclopentane and/or cyclopentene and the method further comprises:

(c) recovering at least part of the cyclopentane and/or cyclopentene and routing to a product disposition and/or recycling at least part of the cyclopentane and/or cyclopentene to the contacting (a).

9. The process of claim 1, wherein the microporous crystalline metallosilicate has a silica to metal molar ratio in excess of 2.

10. The process of claim 1, wherein the microporous crystalline metallosilicate is selected from the group consisting of Zeolite beta, mordenite, faujasite, Zeolite L, ZSM-5, ZSM-11, ZSM-22, ZSM-23, ZSM-35, ZSM-48, ZSM-50, ZSM-57, ZSM-58, MCM-22 family material, and mixtures of two or more thereof.

11. The process of claim 1, wherein the microporous crystalline metallosilicate comprises ZSM-5.

12. The process of claim 1, wherein the conditions employed in the contacting (a) comprise a temperature from 400° C. to 700° C. and a partial pressure of acyclic $C_5$ feedstock from 3 to 100 psia (21 kPa-a to 690 kPa-a) at the reactor inlet.

13. The process of claim 1, wherein the acyclic $C_5$ feed comprises pentane, pentene, pentadiene, and mixtures thereof.

14. The process of claim 1, wherein the acyclic $C_5$ feed comprises at least 75% by weight n-pentane.

15. The process of claim 1, wherein the catalyst composition provides a conversion of at least about 70% of the acyclic C$_5$ feed under conversion conditions including an n-pentane feedstock with equimolar H$_2$, a temperature in the range of about 550° C. to about 600° C., an n-pentane partial pressure from 3 to 30 psia at the reactor inlet (21 kPa-a to 207 kPa-a), and an n-pentane weight hourly space velocity from 5 to 20 hr$^{-1}$.

16. The process of claim 1, wherein the catalyst composition provides a carbon selectivity to cyclic C$_5$ compounds of at least about 30% under conversion conditions including an n-pentane feedstock with equimolar H$_2$, a temperature in the range of about 550° C. to about 600° C., an n-pentane partial pressure from 3 to 30 psia at the reactor inlet (21 kPa-a to 207 kPa-a), and an n-pentane weight hourly space velocity from 5 to 20 hr$^{-1}$.

17. A process for producing cyclic C$_5$ compounds including cyclopentadiene, the process comprising:
(a) contacting a feed containing acyclic C$_5$ hydrocarbons with a catalyst comprising (i) a microporous crystalline metallosilicate having a constraint index less than or equal to 12, (ii) platinum or a compound thereof, and (iii) silver or a compound thereof under conditions effective to convert at least part of the acyclic C$_5$ hydrocarbons in the feed to produce an effluent comprising cyclopentadiene, wherein the microporous crystalline metallosilicate comprises a metallosilicate framework type selected from the group consisting of MWW, MFI, LTL, MOR, BEA, TON, MTW, MTT, FER, MRE, MFS, MEL, DDR, EUO, and FAU; and
(b) recovering cyclopentadiene from the effluent.

18. A process for producing cyclic C$_5$ compounds including cyclopentadiene, the process comprising:
(a) contacting a feed containing acyclic C$_5$ hydrocarbons with a catalyst comprising (i) a microporous crystalline metallosilicate having a constraint index less than or equal to 12, (ii) platinum or a compound thereof, and (iii) copper or a compound thereof under conditions effective to convert at least part of the acyclic C$_5$ hydrocarbons in the feed to produce an effluent comprising cyclopentadiene, wherein the microporous crystalline metallosilicate comprises a metallosilicate framework type selected from the group consisting of MWW, MFI, LTL, MOR, BEA, TON, MTW, MTT, FER, MRE, MFS, MEL, DDR, EUO, and FAU; and
(b) recovering cyclopentadiene from the effluent.

* * * * *